United States Patent
Spruce et al.

(10) Patent No.: US 7,572,762 B1
(45) Date of Patent: Aug. 11, 2009

(54) MATERIALS AND METHODS RELATING TO THE INDUCTION OF APOPTOSIS IN TARGET CELLS

(75) Inventors: Barbara Ann Spruce, Perth (GB); Neil Donald Perkins, Dundee (GB); Jayne Samson, Dundee (GB); Niall McTavish, Tayport (GB)

(73) Assignee: University of Dundee, Dundee (GB)

( * ) Notice: Subject to any disclaimer, the term of this patent is extended or adjusted under 35 U.S.C. 154(b) by 0 days.

(21) Appl. No.: 09/720,851

(22) PCT Filed: Jun. 29, 1999

(86) PCT No.: PCT/GB99/02045

§ 371 (c)(1),
(2), (4) Date: Apr. 6, 2001

(87) PCT Pub. No.: WO00/00599

PCT Pub. Date: Jan. 6, 2000

(30) Foreign Application Priority Data

Jun. 29, 1998  (GB) ................................. 9814036.1

(51) Int. Cl.
*A61K 38/00* (2006.01)
*A61K 31/40* (2006.01)
(52) U.S. Cl. .......................................... 514/2; 514/408
(58) Field of Classification Search ................ 514/279
See application file for complete search history.

(56) References Cited

U.S. PATENT DOCUMENTS 4,795,747 A * 1/1989 Latman et al. ............... 514/182
5,911,970 A * 6/1999 John et al.
6,235,791 B1   5/2001 Breliere

FOREIGN PATENT DOCUMENTS

CH          681780      5/1993
WO    WO 96/06863   *  3/1996

OTHER PUBLICATIONS

Abstract of Ferris et al (Life Sciences, 1986, vol. 38, pp. 2329-2337).*
Abstract of Itoh et al (Naunyn-Schmiededergs Archives of Pharmacology, 1987, vol. 335, pp. 285-289.*
John et al (Journal of Medicinal Chemistry, 1994, vol. 37, pp. 1737-1739.*
Eeles et al (In: Breast Cancer, vol. 18, Eds Fentiman and Taylor-Papadimitriou, 1993, p. 63, Table 3.*
Brent et al (Biochemical and Biophysical Research Communications, 1996, vol. 219, pp. 219-226.*
Abstract of Bigbee (Energy Technology Rev, 1980, pp. 1-8.*
Abstrat of Guzzie (Diss Abstr Int [B], 1988, vol. 8, p. 2201.*
Abstract of Singh (Recent Adv. Cell. Mol. Biol., World Congress, 1992, vol. 2, pp. 117-122.*
Abstract of Kataoka et al (International Journal of Radiation Biology, 1992, vol. 61, pp. 387-392.*
ATCC Accession No. HTB-22.*
The abstract of Moll et al (Hum Pathol, 1995, vol. 26, pp. 1293-1301).*
The abstract of Bours et al (Journal of Cell Biochem, 1995, Suppl 19A, p. 30).*
Verma et al (Nature, 1997, vol. 389, pp. 239-242).*
Eck et al (Gene-Based Therapy, In: The Pharmacological Basis of Therapeutics, Goodman and Gilman, Ed.s, 1996, pp. 77-101).*
Orkin et al ("Report and Recommendation of the Panel to Assess the NIH Investment in Research on Gene Therapy", NIH, 1995).*
The abstract of Littman et al (Archives of Internal Medicine, 1951, vol. 87, pp. 707-712).*
Abstract of Bruger et al (Virchows Archiv fuer Pathologische Anatomie, 1949, vol. 46, pp. 536-541).*
Kleeb et al (LifeSciences, 1996, vol. 60, pp. PL69-PL74).*
Grunberg et al (Journal of Clincial Oncology, 1984, vol. 2, pp. 782-787).*
Silvey et al (Journal of Clinical Oncology, 1988, vol. 6, pp. 1397-1400).*
Vilner et al (The Journal of Neuroscience, 1995, vol. 15, pp. 117-134).*
Mach et al (Cancer Research, 1997, vol. 57, pp. 156-161).*
DeVita et al, 'Hodgkin's Disease' In: Cancer, Principles and Practice of Oncology, DeVita et al, Ed.s, 5th Edition, 1997, pp. 2242-2255.*
Brent, P.J. and G.T. Pang, "Sigma Binding Site Ligands Inhibit Cell Proliferation in Mammary and Colon Carcinoma Cell Lines and Melanoma . . . " Eur. J Pharm., 278:151-160 (1995).

* cited by examiner

*Primary Examiner*—Karen A Canella
(74) *Attorney, Agent, or Firm*—Dann, Dorfman, Herrell & Skillman; Robert C. Netter; Kathleen D. Rigaut

(57) ABSTRACT

Compositions, methods, uses and assemblages for the preferential induction of cell division cycle arrest and/or apoptosis, in a first population of cells compared to a second population of cells employ either: (i) an opioid or opioid-like agent and an NF-κB activating agent, which agents are other than the opioid-like agent trans-U50488 in combination with an NF-κB activating agent selected from etoposide and nocodazole; (ii) a ligand for a sigma receptor, or (iii) an opioid or opioid-like agent wherein the cells of the first population are other than tumor cells.

12 Claims, 30 Drawing Sheets

PE

NFκB p53

PE + NFκB p53 + NFκB

PE + NFκB + p53

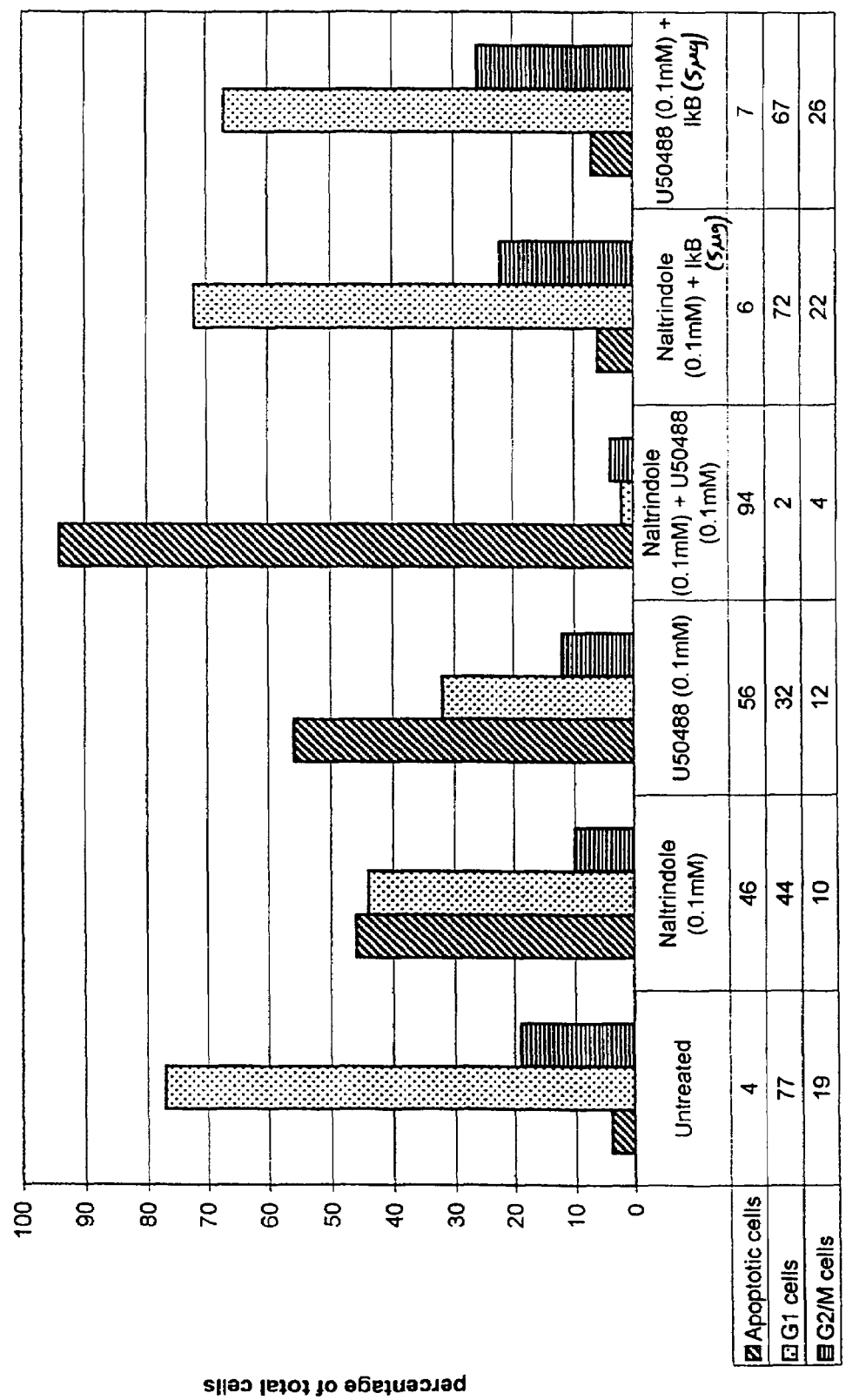

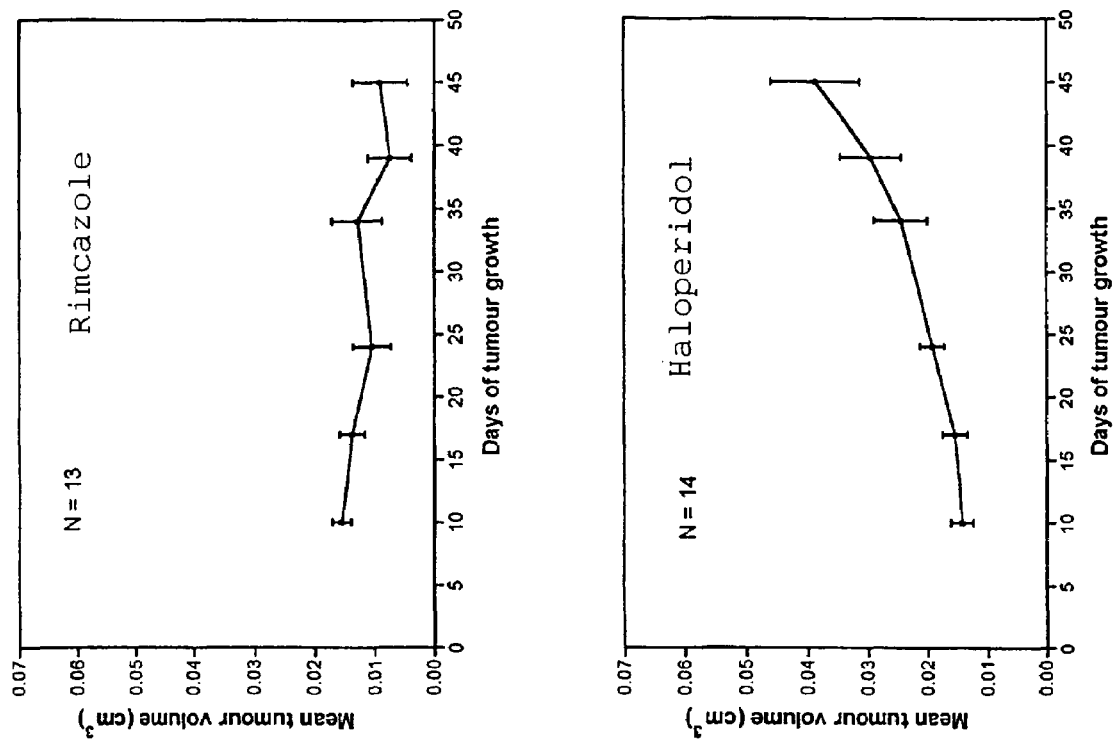
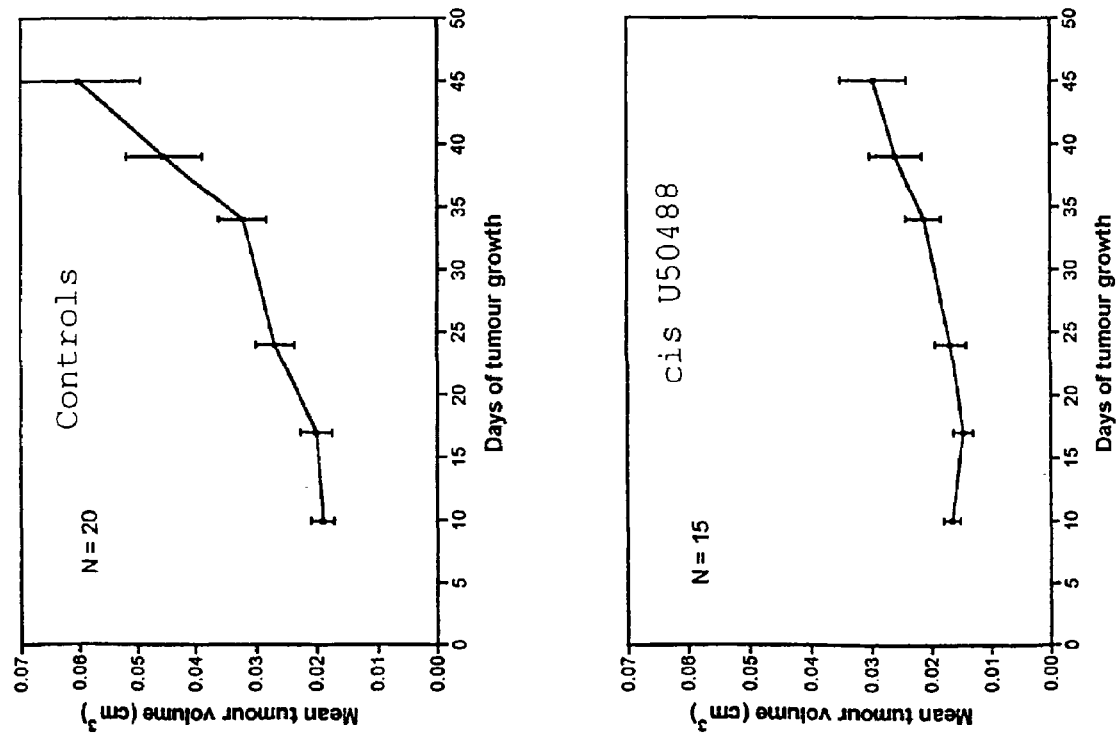
Figure 15a

MATERIALS AND METHODS RELATING TO THE INDUCTION OF APOPTOSIS IN TARGET CELLS

The present invention relates to materials and methods relating to the induction of cell division cycle arrest and/or apoptosis in target cells. In particular the target cells may be tumour cells or cells involved in inflammatory disease processes.

BACKGROUND

It has been proposed that the cell's intrinsic apoptotic death programme provides a crucial restraint on tumourigenesis in at least 2 ways: (1) engagement of the apoptotic death programme in response to non-rectifiable genetic damage prevents potentially oncogenic mutations being passed to subsequent cell generations; (2) an inappropriately proliferating mass of cells engages its death programme when it begins to outstrip its supply of exogenous diffusible and non-diffusible survival signals. The restoration of a defective cell death programme is therefore a goal in tumour therapy.

International Patent Application WO 96/06863, describes opioid-like agents for use in the induction of apoptosis. WO 96/06863 teaches that the behaviour of intracellular proenkephalin is influenced by survival signals which are dependent on cell density and in that way, a line of communication is provided which informs the inside of the cell as to the survival conditions outside the cell. However, it was noted that when cultured rodent fibroblasts (3T3 cells) undergo spontaneous transformation, intracellular proenkephalin immunofluorescence is decoupled from cell density dependent signalling and indeed proenkephalin can be detected even at low cell densities. This behaviour of proenkephalin may allow the transformed cell to disregard the level of external survival signals and so override the death programme in a way beneficial to an early tumour cell mass. Experiments documented in WO 96/06863 showed that dysregulation of endogenous proenkephalin can be mimicked by cytoplasmic proenkephalin expressed from a heterologous promoter. This prevents the cell entering into its death programme in response to agents which normally induce apoptosis. Thus cells where proenkephalin is no longer subject to factors which regulate its expression or activity have a survival advantage which would allow an incipient tumour cell to withstand genetic damage and also to disregard its environment. Thus a pathway in which proenkephalin is involved is a potentially oncogenic pathway which may be widely involved in tumourigenesis.

Cells in a non-transformed state require the continuous provision of several types of survival signals. These are present in the extra-cellular environment in limiting amounts and are usually supplied by neighbouring cells of different types. The survival signals suppress a cell's intrinsic death programme (Raff 1992 Nature Vol. 356 pp 397-400). Thus, the abrogation of a single survival signal would not be anticipated to cause the death of the cell. However, in WO 96/06863 it was taught that if incipient tumour cells acquire a survival advantage due to autonomous upregulation of one pathway, then over a period of time, the clonal mass of cells would become preferentially dependent on that pathway for survival (due to a loss of selective pressure to maintain alternative survival-promoting cell surface receptors, rendered redundant by a depletion of their own signalling molecules normally supplied by cells or matrices of a different type). This was shown by administration of monoclonal anti-proenkephalin antibodies to human cancer cells (in an attempt to abrogate proenkephalin-mediated survival). The result was that apoptosis was induced in tumour cells whereas non-transformed cell lines were less affected. This result supported the prediction that tumour cells would be more susceptible to abrogation of proenkephalin-mediated survival than non-tumour cells.

The identity of extracellular or intracellular proenkephalin receptors is not yet known. However, proenkephalin can be proteolytically cleaved to enkephalin pentapapetides (Met- and Leu-enkephalin) which are known to bind to delta opioid receptors. WO 96/06863 reports on the testing of a synthetic opioid, naltrindole for induction of apoptosis in tumour cells and non-tumour cells. Naltrindole is an antagonist of the delta opioid receptor, the same receptor to which enkephalins bind. Naltrindole was shown to potently induce apoptosis in many human tumour cells with non-tumour cells being less affected. This provided exemplification of preferential dependence of tumour cells on opioid-like pathways for survival.

The applicant also found that an agonistic ligand for the kappa opioid receptor, trans-U50488, is a potent inducer of apoptosis in a wide range of tumour cells and once again, non-tumour cells are less affected. Synergy was also noted between the agents, naltrindole and trans-U50488. Trans-U50488 is a kappa ligand whereas cis-U50488 is a sigma ligand.

Pharmacologists originally subdivided opioid receptors into 4 main classes-mu, delta, kappa, and sigma (for review see Zukin, R. S and Zukin S. R. Trends in Neurosciences 1984 pp 160-164). However, sigma receptors were later regarded as distinct from opioid receptors and to be viewed in a different class. Indeed, this was supported by the cloning of the mu, delta and kappa receptors which showed substantial homology to each other. In contrast, the so-called type 1 sigma receptor shows no significant primary sequence homology to the opioid receptors (see for example Kekuda et al. 1996 Biochem Biophys res Commun Vol. 229, pp 553-558), although additional sigma receptor types remain to be cloned. Evidence has recently emerged that, despite the lack of primary sequence homology, there is some cross-reactivity between sigma and the more "classical" opioid receptors. Kobayashi et al., 1996 Br J Pharmacol Vol 119, pp 73-80 report that sigma receptor ligands (such as cyclazocine, SKF-10047, and haloperidol) can interact with cloned mu-, delta-, and kappa-opioid receptors expressed in Xenopus oocytes. However no evidence exists that sigma ligands interact directly with naturally occurring mu, delta or kappa opioid receptors. Conversely, four different kappa opioid receptor agonists (including trans-U50488, cited in WO96/06863) compete with a sigma-1 receptor ligand to the same extent as sigma-2 ligands (such as haloperidol and rimcazole) for sites in brain, liver and spleen (Brent 1996 Brain Res Vol 725, pp 155-165). A more detailed account of predicted interactions between opiate-related compounds and sigma receptors is given by Walker et al (1990 Pharmacol Rev Vol. 44 pp 355-402). This indicates that among opioid-related compounds, the determinants for sigma receptor activity differ strikingly from the determinants for opiate receptors; also, with opiate-related compounds, the (major subtype of) sigma receptor displays reverse stereo selectivity to the classical opiate receptors.

Sigma receptors are known to be expressed on several different types of tumour cells. For example John et al. 1995 Life Sci Vol. 56, pp 2385-2392, describes sigma receptors on human lung cancer cells; Brent and Pang 1995 Vol. 278, pp 151-160, describes sigma receptors on human breast and colon cancer cells and melanoma cells; Thomas et al. 1990 Life Sci Vol. 46, pp 1279-1286, describes sigma receptors and opioid receptors in human brain tumours. Vilner et al describe sigma receptors in a wide variety of tumour cell lines (Vilner et al, 1995 Cancer Res 55 408-413). Mach et al (Cancer Res 1997 57 156-161) suggest that sigma receptors can be used as markers to assess the proliferative status of a tumour.

Brent and Pang (1995, as above) described the inhibition of tumour cell proliferation by sigma ligands, as has been described for opioid receptor ligands (see for example Maneckjee and Minna PNAS 1992 Vol 89 pp 1169-1173). However, typically, proliferation results in a greater number of cells competing for available survival factors. Thus proliferation is associated with increased apoptosis and conversely an inhibition of cell proliferation is associated with reduced apoptosis. Indeed, Gerard Evan and colleagues proposed obligatory coupling of cell proliferation and cell suicide pathways (see for example Harrington et al Current Opinion in Genetics and Development 1994 Vol 4 pp 120-129.

Brent and colleagues have also described the induction of apoptosis by a sigma receptor ligand, reduced haloperidol in colon and mammary cell lines (Brent et al 1996 Biochem Biophys Res Commun Vol 219 pp 219-225). The natural opium alkaloid noscapine induces apoptosis in tumour cells (Ye et al. 1998 PNAS Vol. 95, pp 1601-16060.) Ye and colleagues also report noscapine-induced regression of human tumour xenografts in mice with little evidence of toxicity and they propose that noscapine depolymerises microtubules.

The transcription factor NF-κB has recently been linked to the control of apoptosis. It is generally regarded as having an anti-apoptotic function. In most cell types, NF-κB is present in the cytoplasm in an inactive form bound to the inhibitor molecule IκB. NF-κB is activated by the removal of the IκB molecule. (See Baeuerle and Baltimore 1996 Cell Vol. 87, pp 13-20 and Baichwal and Baeuerle 1997 Current Biology Vol. 7 pp R94—R96).

Evidence of an anti-apoptotic role for NF-κB includes for example the presence of massive liver cell apoptosis in RelA (p65) (a subunit of NF-κB) knock-out mice (Beg et al. 1995 Nature Vol. 376 pp 167-170). Furthermore, inactivation of NF-κB in B lymphocyte cell lines causes them to apoptose (Wu et al. 1996 EMBO J. Vol. 15 pp 4682-4690). The anti-apoptotic role of NF-κB has been proposed to reduce the efficacy of anti-cancer therapies. Introduction of a "super-repressor" form of IκBα into tumour cells prevents activation of NF-κB. This results in enhanced tumour cell killing in response to a number of anti-cancer agents (Wang et al. 1996 Science Vol. 274 pp 784-786; Antwerp et al. 1996 Science Vol. 274 pp 787-789). Thus a number of cancer therapies including tumour necrosis factor (TNF) alpha, ionising radiation, daunorubicin, etoposide and vincristine are associated with undesirable activation of NF-κB. Beg and Baltimore have gone so far as to deduce that NF-κB is an essential element in the prevention of TNF-α-induced death (1996 Science Vol. 274 pp 782-784). As a result, there is much current interest in the possibility that prevention of NF-κB activation will enhance tumour cell responsiveness to a wide range of anti-cancer agents (see overview by Barinaga Science 1996 Vol 274 p724).

In some situations and cell types there is suggestion of a pro-apoptotic function of NF-κB. For example, serum starvation of 293 cells causes cell death which is blocked by a dominant negative form of RelA (Grimm et al. 1996 J. Cell Biol. Vol. 134, pp 13-23) and also radiation-induced apoptosis in fibroblasts from ataxia telangiectasia patients is reduced by "super-repressor" IκBα which prevents NF-κB activation (Jung et al 1995 Science Vol. 268 pp 1619-1621). Thus, the relationship of NF-κB to the control of apoptosis is unclear, with little immediate prospect of understanding how a cell decides to engage anti- or pro-apoptotic outcomes in response to NF-κB.

NF-κB has been linked to the genesis and progression of tumours. For example, disruption of IκBα leads to malignant transformation of 3T3 cells (Beauparlane 1994 Oncogene Vol 9 pp 3189-3197) and the absence of functional IκBα protein leads to constitutively active NF-κB in Hodgkins lymphoma lines (Wood et al. 1998 Oncogene Vol. 16, pp 2131-2139). A reciprocal relationship between NF-κB and the tumour suppressor p53 has also been shown (N. Perkins, unpublished). Constitutive activation of NF-κB has also been linked with progression of breast cancer to hormone-independent growth (Nakshatri et al. Mol. Cell. Biol. 1997 Vol. 17 pp 3629-3639). Thus the inappropriate activation of NF-κB in tumours points towards a therapeutic approach which neutralises or inhibits the activity of NF-κB.

However, global abrogation of NF-κB activity would reduce its pro as well as its anti apoptotic effects and would therefore be less effective than, for example, selective abrogation of the anti apoptotic effects. Further, none of the studies which describe an enhanced apoptotic effect of anti-cancer agents when NF-κB is inhibited, show a preferential effect on tumour compared to non-tumour cells (Barinaga Science 1996 Vol. 274 p 724).

There is some evidence for a link between the NF-κB and opioid pathways. For example, NF-κB activates transcription of the proenkephalin gene in T lymphocytes (Rattner et al. 1991 Mol. Cell. Biol. Vol 11 pp 1017-1022). The regulatory region of the delta opioid receptor gene also contains an element to which NF-κB would be expected to bind (Augustin et al 1995 Biochem Biophy Res Commun Vol. 207 pp 111-119).

Also, stimulation of the mu opioid receptor results in activation of NF-κB in cultured neurons (Hou at al 1996 Neurosci Letts Vol 212 pp 159-162). These results do not however suggest that opioids will modulate the outcome of NF-κB activation.

Features shared by cells undergoing apoptosis and mitosis, such as chromosome condensation and nuclear lamina disassembly, led at one time to the proposal that apoptosis is a form of aberrant mitosis (Earnshaw 1995 Curr Op Cell Biol Vol 7 pp 337-343). This view was supported by an observation of the necessity for active p34$^{cdc2}$ kinase, an enzyme universally required for entry into mitosis, in apoptotic death induced by treatment with perforin and fragmentin-2 (Shi et al 1994 Science Vol 263 pp 1143-1145). In contrast, other studies showed apoptosis unaccompanied by activation of p34$^{cdc2}$ (Norbury et al. 1994 Biochem Biophys Res Commun Vol. 202 pp 1400-1406; Oberhammer et al 1994 J Cell Biol Vol 126 pp 827-837). These conflicting data led to the conclusion that the resemblance between apoptosis and mitosis is coincidental (see Earnshaw review 1995).

On the other hand, a connection between decision-making events in proliferation and cell death control remains widely accepted (see review by Gerard Evan and colleagues: Harrington et al 1994 Curr Op Genetics and Dev. Vol 4, pp 120-129). It has been proposed that an obligate coupling between the cell death programme and cellular proliferation provide a crucial brake on tumorigenesis. For example, c-Myc, a molecule essential for cell proliferation, promotes cell death instead of cell proliferation when exogenous survival factors become limiting (Evan et al 1992 Cell vol 63 pp 119-125). A proliferating mass of cells which outstrips its supply of exogenous survival factors will die by apoptosis unless it has acquired the ability to survive by self-generated factors. This connection predicts therefore that a reduction in cellular proliferation will be accompanied by a reduction in the cell's propensity to undergo apoptosis.

Apoptosis in response to opioid-like agents is preceded by an induction of mitotic arrest (Ye et al PNAS 1998 Vol 95 pp 1601-1606). This is not a common pathway to apoptosis induction.

Evidence for this as an opioid-dependent mechanism of apoptosis induction was provided in WO 96/06863 which disclosed that proenkephalin antibodies induced entry into mitosis but with failure of mitotic progression. However, a connection between mitotic arrest and apoptosis induction could not have been predicted at the time.

Activated NF-κB is proposed to play a role in both chronic and acute inflammation (Baldwin 1996 Annu Rev Immunol Vol 14 pp 649-681). For example NF-κB is activated in arthritic synovium and anti-arthritic therapies block NF-κB activation. Acute inflammation such as septic shock is also associated with NF-κB activation. A number of chronic diseases are not obviously inflammatory in nature, but inflammatory mechanisms may play a part. For example, autoimmune diseases such as systemic lupus erythematosus, atherosclerosis and Alzheimer's disease are all reported to be associated with NF-κB activation.

Haslett (1997 British Medical Bulletin Vol 53 pp 669-683) discovered some years ago that inflammatory cells undergo apoptosis constitutively and proposed that elimination of inflammatory cells by apoptosis is a crucial mechanism to limit the inflammatory response and that a failure of this mechanism leads to persistent inflammation. Molecules or pathways which inappropriately extend the lifespan of inflammatory cells, through delay in engagement of their constitutive death programme, have yet to be identified.

The reduction of NF-κB activity is a goal of workers attempting to discover therapies for inflammatory and associated disorders.

The present inventors have now discovered that ligands which bind opioid receptors or relatives of opioid receptors induce apoptosis preferentially in tumour cells as compared to non-tumour cells, a property which was described in WO96/06863 for two named ligands, trans-U50488 and naltrindole. However, the present inventors now show that these ligands induce apoptosis through an NF-κB-dependent mechanism and that this is at least partly consequent on arrest in mitosis (possibly through microtubule disruption). This NF-κB dependent mechanism, which involves switching activated NF-κB into a pro-apoptotic mode, has not been previously disclosed.

The results herein also show that the apoptotic effect which relies on activated NF-κB is greater on tumour cells (particularly those when NF-κB is constitutively active) than on non-tumour cells.

Prevailing scientific opinion indicates that the apoptotic effect of anti-cancer agents is enhanced by the inhibition of NF-κB. In contrast the present application demonstrates that opioid-mediated conversion of activated NF-κB from anti- to a pro-apoptotic role can be used to enhance the efficiency of certain anti-cancer agents (e.g. TNF).

This approach is contrary to the prevailing scientific opinion in the field.

In WO96/06863, a powerful cooperative effect (specifically, an acceleration of the onset of the death programme) between opioids and nocodazole was described. However, disclosure of the present application allows for the first time the skilled person to predict specifically that agents which depolymerise microtubules (such as colchicine, nocodazole, podophyllotoxin and vinblastine, particularly since Ye et al describe noscapine binding sites on tubulin to be distinct) will cooperate with opioid—like compounds in apoptosis induction through activation of NF-κB.

The provision of a pro-apoptotic switch, to activated NF-κB, by a number of opioid-like compounds, including noscapine, explains the apoptotic fate of cells in which microtubules have been depolymerised by noscapine. However, the cooperation of opioids with NF-κB B to induce death is not reliant on microtubule depolymerisation as the stimulus to NF-κB activation.

The phenomenon of apoptosis preceded by mitotic arrest is shared by noscapine and other opioid-like agents. Given that there is no universal connection between apoptosis and mitotic arrest, this indicates that opioid-like pathways, including those in which noscapine participates, are inducing apoptosis through a similar mechanism which is otherwise uncommon.

Induction of apoptosis by opioid-like agents is not necessarily consequent upon mitotic arrest. Data herein for example with tumour necrosis factor (TNF), show that agents which induce activation of NF-κB in a microtubule-independent manner also cooperate with opioids to induce apoptosis and that the cooperativity is blocked by IκB. Thus, the pro-apoptotic switch provided to activated NF-κB by opioid-like agents is not exclusively dependent on microtubule depolymerisation effects.

The disclosure of Ye et al contains no suggestion of how noscapine may be gaining access to the interior of the cell. Noscapine-binds with high affinity (in the nanomolar range) to brain-specific non-opioid sites (Mourey et al. 1992 Mol Pharmacol Vol. 42, pp 619-626) which leaves open the question of what, if any, receptors noscapine is binding to on the surface of tumour cells.

Kamei and colleagues (Kamei et al Eur J Pharmacol 1993 Vol. 242, pp 209-211, and Kamei Pulm Pharmacol 1996 Vol. 9, 349-356) describe that the anti-tussive effects of noscapine are significantly reduced by pre-treatment with rimcazole, a specific antagonist of sigma site; The conclusion is that sigma sites may be involved in the anti-tussive mechanism of non-narcotic anti-tussive drugs (such as noscapine and dextromethorphan). This data suggests some indirect cross talk between the two receptor systems, rather than direct cross reaction of noscapine with sigma receptors.

However, the high dose of noscapine (120 mg/kg by intraperitoneal administration to mice) described by Ye et al to be required for induction of apoptosis and tumour regression is substantially higher than the dose required (10 mg/kg intraperitoneally) to produce an anti-tussive effect. From this teaching the skilled person could not deduce that the anti-tumour effect of noscapine is mediated through sigma receptors on the cell surface. Indeed, Ye and colleagues show an intracellular microtubule depolymerising effect of noscapine, due, they propose, to a fortuitous structural similarity between noscapine, colchicine and podophyllotoxin which are known microtubule depolymerising agents and have no known affinity for cell surface or intracellular opioid or sigma receptors.

This application shows that noscapine, surprisingly, shares the same mechanism of apoptosis induction in tumour cells as opioid receptor ligands and sigma receptor ligands. The inventors now demonstrate that tumour cells in which NF-κB is constitutively activated are particularly susceptible to noscapine. They also demonstrate that noscapine cooperates with exogenous activators of NF-κB in tumours where NF-κB is not known to be constitutively active.

It is known that opioid receptors can be internalised after ligand binding by an endocytic mechanism. In this way, ligands can be delivered to the interior of the cell (Keith et al.

1998 Mol. Pharmacol. Vol 53, pp 377-384). The present inventors propose that noscapine is gaining access to the interior of the cell, and thence to microtubules, after binding to opioid-like receptors on the cell surface. Microtubule depolymerisation is a known stimulus to NF-κB activation (Rosette and Karin 1995 J. Cell Biol. Vol 128 6 pp 1111-1119) but this would not in itself be a sufficient explanation for apoptosis induction by noscapine since NF-κB activation generally provides an anti-apoptotic effect (see below). The present application shows that noscapine, opioid and sigma ligands use the same, otherwise uncommon, mechanism to induce apoptosis. Namely the provision of a pro-apoptotic switch to activated NF-κB at least partly through microtubule depolymerisation.

The present application explains why noscapine has an unexpected pro-apoptotic effect, since it provides a pro-apoptotic switch to activated NF-κB. In the examples it is shown that blockade of NF-κB activation by IκB blocks noscapine and other opioid-induced death. The inventors show that proliferating non-tumour cells retain correct cell cycle checkpoint control in the present of opioids (see exemplification). This provides a further mechanism for enhanced toxicity in tumour compared to non-tumour cells.

The present invention also addresses the role of sigma ligands in inducing apoptosis in tumour cells and provides evidence that such ligands employ the same novel NF-κB dependent mechanism of apoptosis induction as conventional opioid receptor ligands. Walker et al (1990 Pharmacol. Rev. Vol. 42 pp 335-402) comment that the sigma receptor displays reverse stereo selectivity to the classical opioid receptors. Of particular relevance, cis-isomers of U50488 bind to sigma receptors whereas trans-isomers of U50488 bind to kappa receptors. In the experiments of WO96/06863, the trans-isomer of U50488 (Sigma Chemical Company D-8040; trans-3,4-dichloro-N-methyl-N-(2[1-pyrrolidinyl]cyclohexyl)-benzeneacetamide) which binds kappa receptors in preference to sigma receptors, is used. Different isomers of benzomorphans also prefer to bind either kappa or sigma receptors. Thus, in two unrelated classes of compounds, different isomers show preferences for kappa or sigma receptors. Walker comments that this suggests a possible relationship between the topography of the kappa opiate and sigma receptor binding sites. A cooperative functional interaction between kappa and sigma binding sites is taught herein. It is shown that the sigma ligand rimcazole cooperates with a trans-isomer of U50488 (a kappa ligand) in the induction of apoptosis in cancer cells (FIG. 10b).

Brent et al (1996 Brain Res Vol 725, pp 155-165) describe that kappa opioid receptor agonists, including trans-U50488, moderately inhibit sigma-1 receptor binding in guinea pig brain, liver and spleen. However, Brent present no evidence that kappa agonists interact directly with sigma receptors. An explanation for his data would be that kappa receptors are coupled, perhaps by heteroligomerisation, to sigma receptors. Another explanation would be that a distinct kappa-like binding pocket is allosterically coupled to a sigma binding pocket, within the same receptor macromolecule. In that way, kappa ligands could indirectly affect the binding of specific sigma ligands. Furthermore, there is no evidence presented by Brent that kappa ligands affect the binding of sigma ligands to human tumour cells. In the present application the role of sigma ligands in inducing apoptosis preferentially in tumour compared to non-tumour cells is specifically addressed and it is shown that sigma ligand-induced apoptosis is mediated at least in part by the same intracellular NF-κB-dependent events as more conventional opioid receptor ligands. The elucidation of this common mechanism has allowed the present inventors to predict, and exemplify, that apoptosis is preferentially induced in tumour compared to non-tumour cells. Tumour cells in which NF-κB is constitutively activated are particularly susceptible; otherwise, the sigma ligands can be co-administered with exogenous activators of NF-κB, as is proposed for opioid receptor ligands.

Brent and colleagues have also described the induction of apoptosis by a sigma receptor ligand, reduced haloperidol, in colon and mammary carcinoma cell lines (Brent et al 1996 Biochem Biophys Res Commun Vol. 219 pp 219-226). The demonstration of apoptosis induction per se does not in itself predict application of an agents to anti-cancer therapy since there are many hundreds of agents which induce apoptosis in cells but do so to the same extent in diseased compared to non-diseased cells; hence, any application to an in vivo situation would be predicted to be fatal. Thus, a crucial feature of an apoptosis-inducing agent of likely therapeutic ability is a clear preference to induce apoptosis in diseased compared to non-diseased cells. This is shown in the present application. A more recent paper on the potential applicability of sigma ligands to cancer management is in the area of diagnostics rather than therapy. Specifically, Mach and colleagues (Cancer Res. 1997 Vol. 57 pp 156-161) acknowledge that the function of sigma receptors on tumour cells is unknown, but suggest that sigma ligands may be used as markers to assess the proliferative status in tumours. No suggestion is made that they may be therapeutically important in their own right.

Opioids are also beneficial in providing a pro-apoptotic switch to activated NF-κB in chronically inflamed cells, thereby contributing to a resolution of the inflammatory process. An inappropriate NF-κB mediated drive to survive in chronic inflammation, which is apparent through the extended average life span of inflammatory cells, leads to a loss of selective pressure to maintain alternative survival pathways over successive inflammatory cell generations. Inflamed cells under these conditions become locked into a dependence on one pathway for survival, in an analogous way to tumour cells. Global inhibition of NF-κB activity is one potential therapeutic strategy because it would be more effective in chronically diseased cells which have been reliant on NF-κB for survival. However, the duplicitous nature of NF-κB means that the effect of this approach might be offset by a reduction in an associated NF-κB mediated pro-apoptotic drive (i.e. chronically inflamed cells also exist on a knife-edge between life and death in the same way proposed for tumour cells). An alternative and entirely novel strategy would therefore be to provide a pro-apoptotic switch to activated NF-κB using opioid-like pathways. This strategy would not necessarily rely on the presence of opioid receptors on inflammatory cells since therapies can employ agents linked to internalisation peptides such as "Penetrating" as was described in WO96/05863.

According to a first aspect of the present invention there is provided a composition for the preferential induction of cell division cycle arrest and/or apoptosis, in a first population of cells compared to a second population of cells which composition comprises an opioid or an opioid-like agent and an NF-κB activating agent, which agents are other than the opioid-like agent trans-U50488 in combination with an NF-κB activating agent selected from etoposide and nocodazole.

The cells of the first population, compared to cells of the second population, may be referred to herein as "abnormal" and/or "undesirable" cells. The cells of the second population are preferably normal and/or desirable cells within the context of the intended use of the invention, for example cells which do not display characteristics typically associated with a disease or condition which is intended to be treated using the invention. In particular the cells of the first population are preferably tumour cells or undesirable cells of an inflammatory process and the cells of the second population are preferably non-tumour and/or non-inflammatory cells.

The phrase "cell division cycle arrest" is intended to mean that the cells in the population fail to increase in number over time.

The abnormal and/or undesirable cells may in some instances have a preferential dependance for survival on the pathways in which products of opioid peptide precursor and/or sigma receptor genes participate.

An opioid-like agent is a ligand which is capable of binding to one or more receptors of the mu opioid receptor, the delta opioid receptor, the kappa opioid receptor or the sigma receptor class or to another receptor capable of binding known ligands for the mu, delta, kappa and sigma receptors. Thus an opioid-like agent may be a ligand as stated above which can bind one or more of said receptors with moderate to high affinity defined according to standard pharmacological principles (see for example review by Walker et al., 1990 Pharmacologica Reviews Vol. 42 pp 355-400).

Examples of opioid-like agents according to the present invention include proenkephalin; derivatives of proenkephalin (such as met- and leu-enkephalin); noscapine; kappa receptor agonists (such as trans-U50488, bremazocine, spirodoline, ICI 197067, (−)-pentazocine, (−)-ethylketocyclazocine, (−)-cyclazocine and (−)—N-allylnormetazocine ((−)-SKF10,047)); delta receptor antagonists (such as naltrindole); and sigma receptor ligands (such as haloperidol, reduced haloperidol, rimcazole, 1,3-di (2-tolyl) guanidine, (+)-N-allyl normetazocine, (+)-pentazocine, (+)-ethylketocyclazocine, (+)-benzomorphans such as (+)-pentazocine and (+)-ethylketocyclazocine, (+)-morphinans such as dextrallorphan, cis-isomers of U50488 and analogues, arylcyclohexamines such as PCP, N-N'-diryl-substituted guanidines such as DTG, phenylpiperidines such as (+)-3-PPP and OHBQs, steroids such as progesterone and desoxycorticosterone, butryophenones, BD614, (+/−)-cis-N-methyl-N-[2-(3,4-dichlorophenyl)ethyl]-2-(1-pyrrolodinyl)cyclohexylamine, antipsychotic and potential antipsychotic drugs, additional to haloperidol and rimcazole, which bind with a moderate to high degree of potency to sigma sites including: perphenazine, fluphenazine, (−)-butaclamol, acetophenazine, trifluoperazine, molindone, pimozide, thioridazine, chlorpromazine and triflupromazine, BMY 14802, BMY 13980, remoxipride, tiospirone, cinuperone (HR 375), WY47384; antidepressants including amitriptyline and imipramine; see e.g. Walker et al 1990 Pharmacological Reviews Vol. 42 p 355-400).

The above mentioned compounds are exemplary opioid-like agents. Others may be readily ascertained by those skilled in the art, based on the above described binding characteristics.

Generally speaking kappa agonists are those agents which preferentially stimulate activity at kappa opioid receptors when tested against other opioid receptor types. Delta antagonists are those agents which preferentially antagonise the activity of delta opioid receptors when tested against other opioid receptor types. Sigma ligands are those agents which preferentially bind to sigma receptors when tested against other opioid receptor types. A ligand for a sigma receptor for use in accordance with the invention can be identified by the following method (Vilner et al Cancer Res 1995 55:2 408-413).

Firstly, a suitable preparation such as a crude membrane portion is made, by conventional protocols, from a cell type, such as a human tumour cell line, which is known to express sigma receptors. Examples of such cell lines would include; A375 melanoma (Accession No: ECACC 88113005), SK-N-SH neuroblastoma (Accession No: ECACC 86012802) and LNCaP.FGC prostate (Accession No: ECACC 89110211). These cell lines are obtainable from the European Collection of Animal Cell Cultures (Porton Down, England) with reference to the accession numbers shown.

The binding of a putative sigma ligand to sites on these preparations is then measured in comparison to the prototypic sigma ligands such as (+)-pentazocine and 1,3-di-o-tolylguanidine (DTG) (and as described by Walker et al., 1990 Pharmacologica Reviews Vol. 42 pp 355-400). Radio or chemically labelled prototype sigma ligands are allowed to bind to sigma receptors in the cell preparation. The amount of labelled prototype sigma ligand displaced by the putative ligand is measured and used to calculate the affinity of the putative ligand for the sigma receptor.

An NF-κB activating agent is any agent capable of activating NF-κB. Examples of NF-κB activators suitable for use according to the present invention can include; cytokines, mitogens, prostaglandins, leukotrienes, bacteria, bacterial proteins, viruses, viral proteins, chemical agents, oxidising agents, microtubule depolymerising agents (such as colchicine, nocodazole, podophyllotoxin and vinblastine), genotoxins (such as etoposide) and the RelA(p65) subunit of NF-κB or agents which cause its expression, overexpression or activation (e.g. an expression vector for RelA(p65) or a transcription factor which causes its upregulation or an agent which induces its translocation to the cell nucleus). Further exemplary agents are named in the following table (From Siebenlist et al 1994 Annu. Rev. Cell Biol. 10 405-455).

| | |
|---|---|
| Cytokines | Tumour necrosis factor-α (TNF-α) |
| | Lymphotoxin (LT) (TNF-β) |
| | Interleukin-1 α and β (IL-I α and β) |
| | Interleukin-2 (IL-2) |
| | Leukemia Inhibitory factor (LIF) |
| | (Interferon-γ) |
| | (Macrophage colony-stimulating factor (M-CSF) |
| | (Granulocyte/macrophage colony-stimulating factor) (GM-CSF) |
| Mitogens | Antigen |
| | Allogenic Stimulation |
| | Lectins (PHA, Con A) |
| | anti-αβ T cell receptor |
| | anti-CD3 |
| | anti CD2 |
| | anti-CD28 |
| | Phorbol esters |
| | (Diacylglycerol (DAG) |
| | Calcium ionophores (ionomycin, A2837) |
| | anti-surface lgM |
| | (P39) (CD-40 ligand) |
| | Serum |
| | (Platelet-derived growth factor) (PDGF) |
| Other biological mediators | Leukotriene B4 |
| | (Prostaglandin E2 (PGE2) |
| | (Insulin) |
| Bacteria and bacterial products | *Shigella flexneri* |
| | *Mycobacterium tuberculosis* |
| | Cell wall products: |
| | Lipopolysaccharide (LPS) |
| | Muramyl peptides |
| | (G(Anh)MTetra) |
| | Toxins: |
| | *Staphylococcus* enterotoxin A and B (SEA and SEB) |
| | Toxic shock syndrome toxin-1 (TSST-1) |
| | (Cholera toxin) |

-continued

| | |
|---|---|
| Viruses and viral products | Human T cell leukemia virus-l (HTLV-1)<br>Tax<br>Hepatitis B virus (HBV)<br>Hbx<br>MHBs<br>Epstein-Barr virus (EBV)<br>EBNA-2<br>LMP<br>Cytomegalovirus (CMV)<br>(Human immunodeficiency virus-1) (HIV-1)<br>Human herpes virus-6 (HHV-6)<br>Newcastle disease virus<br>Sendai virus<br>Adenovirus 5<br>ds RNA |
| Eukaryotic parasite | *Theileria parva* |
| Physical stress | UV light<br>Ionizing radiations (X and γ)<br>(Photofrin plus red light)<br>(Hypoxia)<br>Partial hepatectomy |
| Oxidative stress | Hydrogen peroxide<br>Butyl peroxide<br>Oxidised lipids<br>(Antimycin A) |
| Chemical agents | Calyculin A<br>Okadaic acid<br>(Pervanadate)<br>(Ceramide)<br>(Dibutyrl c-AMP)<br>(Forskolin)<br>Protein synthesis inhibitors<br>Cycloheximide<br>Anisomycin<br>Emetine |

The composition may be in the form of a pharmaceutical. The composition may be for the preferential induction of cell division cycle arrest and/or apoptosis, in abnormal and/or undesirable cells of a particular tissue type, in which case the NF-κB activating agent may have the requisite tissue specificity. For example the NF-κB activator CD40 ligand is specific for lymphoid tissue.

Pharmaceutical compositions according to the present invention, may include, in addition to active ingredient, a pharmaceutically acceptable excipient, carrier, buffer, stabilised or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

The present invention also provides a method for the preferential induction of cell division cycle arrest and/or apoptosis, in a first population of cells compared to a second population of cells, which comprises exposing cells to an opioid or an opioid-like agent and an NF-κB activating agent, which agents are other than the opioid-like agent trans-U50488 and an NF-κB activating agent selected from etoposide and nocodazole. The populations of cells may be as stated above. "Opioid-like agent", and "NF-κB activating agent" are as defined and explained above.

The method may be employed ex vivo or in the treatment of a patient, in which case pharmaceutical composition according to the invention may be administered to the patient. Alternatively the patient may be treated with ionising radiation or U-V light (see table) to activate NF-κB in target cells combined with administration of a pharmaceutical composition comprising an opioid or opioid-like agent.

The method may be for the preferential induction of cell division cycle arrest and/or apoptosis, of cells of a particular cell type, in which case use may be made of an NF-κB activating agent which has the requisite tissue specificity. For example for preferential induction of cell division cycle arrest and/or apoptosis, in abnormal and/or undesirable cells in lymphoid tissue, CD40 ligand may be employed as the activator of NF-κB.

Administration of a pharmaceutical composition according to the invention or radiation/U-V light and a pharmaceutical composition comprising an opioid or opioid-like agent is in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

The treatment in accordance with the present invention may be given alone or in combination with other treatments, either simultaneously or sequentially dependent upon the condition to be treated.

The present invention also provides a method for the preparation of a composition for the preferential induction of cell division cycle arrest and/or apoptosis, in a first population of cells compared to a second population of cells which method comprises selecting an agent for its ability to activate NF-κB and combining this NF-κB-activating agent with an opioid or opioid-like receptor ligand. The present invention also provides a method for the preferential induction of cell division cycle arrest and/or apoptosis, in a first population of cells compared to a second population of cells which comprises selecting an agent for its ability to activate NF-κB and exposing cells to this NF-κB activating agent and to an opioid or opioid-like receptor ligand. The cells, "opioid-like agent" and "NF-κB activating agent" are all as stated and explained above. A tissue-specific activating of NF-κB may be selected.

The present invention also provides use of an NF-κB activating agent and an opioid or opioid-like receptor ligand in the preparation of a composition for the preferential induction of cell division cycle arrest and/or apoptosis, in a first population of cells compared to a second population of cells. The use may be in relation to the preparation of a pharmaceutical composition. The use may be in relation to the preparation of a pharmaceutical composition for the treatment of tumours.

The use may be in relation to the preparation of a pharmaceutical composition for the treatment of undesirable inflammation.

Similarly the present invention provides use of an NF-κB activating agent and an opioid or opioid-like receptor ligand in the design of a treatment regime for the preferential induction of cell division cycle arrest and/or apoptosis, in a first population of cells compared to a second population of cells. The treatment regime may be in relation to the treatment of tumours or undesirable inflammation. The use may be of a tissue-specific NF-κB activating agent.

The present invention also provides an assemblage of a composition as disclosed above with direction instructing administration of the composition in a manner which results in the preferential induction of cell division cycle arrest and/or apoptosis, in a first population of cells compared to a second population of cells. Thus the present invention provides an assemblage of a composition as disclosed above with directions instructing administration of the composition to a patient with or at risk of a tumour or to a patient with or at risk of an undesirable inflammation.

In some instances the cells of the first population may in terms of function be p53 null tumour cells. In other instances the cells of the first population may in terms of function be p53 wild-type tumour cells. Compositions, methods and uses as set forth above which employ an NF-κB activating agent and an opioid or an opioid-like receptor ligand and composition, methods and uses as set forth above which employ a ligand for a sigma receptor may also employ p53 or an agent which causes expression, overexpression and/or activation of p53 (such as an expression vector for or agent causing upregulation of p53). The present inventors demonstrate herein powerful cooperativity between sigma ligands and p53 using three different systems. Furthermore, the sigma ligands are effective in the nanomolar range, providing strong evidence that the apoptotic effect is mediated through authentic sigma receptors.

According to another aspect of the present invention there is provided a composition for the preferential induction of cell division cycle arrest and/or apoptosis, in a first population of cells compared to a second population of cells, which composition comprises a ligand for a sigma receptor. "Sigma receptor ligands" are as defined and explained above. The cells are as stated above and may be tumour cells or undesirable cells of an inflammatory process. Examples of sigma receptor ligands are stated above. The composition may be in the form of a pharmaceutical. The pharmaceutical may take a general form as described above.

The present invention also provides a method for the preferential induction of cell division cycle arrest and/or apoptosis, in a first population of cells compared to a second population of cells which comprises exposing cells to a ligand for a sigma receptor. The method may be employed to treat a patient or may be ex vivo. The method may comprise the administration of a pharmaceutical composition as provided above wherein the effective agent is a sigma receptor ligand. The present invention also provides a method for the preparation of a composition for the preferential induction of cell division cycle arrest and/or apoptosis, in a first population of cells compared to a second population of cells which method comprises incorporating a ligand of a sigma receptor into the composition. The method may comprise the preparation of a pharmaceutical composition.

The present invention also provides an assemblage of a composition as above comprising a ligand for a sigma receptor with directions instructing administration of the composition in a manner which results in the preferential induction of cell division cycle arrest and/or apoptosis, in a first population of cells compared to a second population of cells. The instructions may direct administration of the composition to a patient with or at risk of a tumour as to a patient with or at risk of an undesirable inflammation.

Compositions, methods and uses as set forth above which employ a ligand for a sigma receptor may also employ as an effective agent an agonist for a kappa receptor. Kappa agonists are as stated and explained above. Exemplary kappa agonists are also mentioned above.

Composition, methods and uses as set forth above may be employed in relation to situations e.g. medical conditions/disease states characterised by dysfunctional regulation of NF-κB, the dysfunctional regulation being characterised by one or more of the following: the presence of constitutively activated NF-κB in cells where it would not normally be found, activation of NF-κB to supranormal levels and/or with an abnormally long duration of activation following cellular stimulation, and the presence of activated NF-κB which has an abnormal subunit composition.

The present invention also provides a composition, and corresponding methods and uses as set forth for previous aspects of the invention, for the preferential induction of cell division cycle arrest and/or apoptosis, in a first population of cells compared to a second population of cells which composition comprises an opioid or an opioid-like agent (i.e. an NF-κB activating agent need not be present) wherein the cells of the first population are other than tumour cells. Such cells may be characteristic of an inflammatory disease (ie a disease where inflammation plays a role), arthritis, atherosclerosis, Alzheimer's disease, multiple sclerosis, autoimmune disease.

The cells of the first population may in some such instances have a preferential dependance for survival on the pathways in which products of opioid peptide precursor and/or sigma receptor genes participate.

Where more than one agent or ligand as defined herein is used in accordance with the invention in any of its aspects, at least one and preferably all is/are present or used in a sublethal amount, i.e. an amount insufficient for that ligand or agent alone to induce inhibition of the cell division cycle and/or apoptosis in a substantial proportion of target cells such that those cells fail to recover viability. Such use can have the advantage of reduced toxicity of the agents or ligands to non-target cells.

Appendix 1 at the end of the examples provides IUPAC chemical names for 1) named agents which induce apoptosis and 2) prototypic sigma ligands for assays to ascertain sigma agents.

FIGURES

FIG. 8 illustrates a representative FACS (fluorescence activated cell sorting) profile obtained from the experiment indicated; horizontal axis denote DNA content of the cells and the vertical axis the numbers of cells that have a particular DNA content. Apoptotic cells have a subnormal DNA content and are represented as a peak to the extreme left of the profile (sub-G1); viable cells are represented in G1 and G2/M peaks which correspond to these phases of the cell cycle. Where percentages are provided, these indicate cells in sub-G1, G1 or G2/M phases, as indicated, as a percent of the total cell population. In all cases, the existence of apoptotic cells was confirmed by additional means such as microscopic examination.

Bar charts show quantitative data obtained from representative FACS analyses for the experiments indicated. In all cases, numbers of cells that are apoptotic (sub-G1), as a percentage of the total cell population, are depicted by diagonal-hatched bars; numbers of cells that are viable and in G1 (G1/S) phase of the cell cycle, as a percentage of the total cell population, are depicted by stippled bars; viable cells in G2/M phase of the cell cycle are depicted by horizontal-hatched bars.

FIG. 1

Quantitative representation of FACS analysis showing cooperation of opioids (Naltrindole) with TNF in apoptosis induction and its diminution when NF-κB is inhibited by IκB.

FIG. 2

Quantitative representation of FACS analysis showing the cooperation of proenkephalin with TNF in NFκB-dependent apoptosis induction in 293 cells.

FIG. 3

Quantitative representation of FACS analysis showing cooperation between Noscapine and TNF in apoptosis induction in p53 null lung carcinoma (H1299) cells.

FIG. 4

Quantitative representation of FACS analysis showing cooperation of Noscapine and TNF in inducing apoptosis in human colon carcinoma (HT29) cells.

FIG. 5

Phase micrographs of 293 cells transiently transfected with a DNA expression vector encoding nuclear proenkephalin showing apoptotic induction in combination with the p65 (RelA) subunit of NF-κB and more markedly when proenkephalin is in triple combination with p65(RelA) and p53.

FIG. 6

Quantitative representation of FACS analysis of 293 cells showing apoptotic induction with trans-U50488 and Naltrindole alone, and synergistically when in combination; and a marked reduction in opioid-induced apoptosis with a repressor of NF-κB (IκB).

FIG. 7a

Quantitative representation of FACS analysis of L428 Hodgkins lymphoma cells showing induction of apoptosis at 0.1 mM Naltrindole and 0.1 mM Noscapine and the induction of apoptosis and cell cycle (G2/M) arrest at 0.01 mm Naltrindole and 0.1 mM Noscapine.

FIG. 7b

Quantitative representation of FACS analysis of Control B lymphoid cells showing the absence of any effect of Naltrindole at 0.1 mM or 0.01 mM or Noscapine at 0.1 mM or 0.01 mM, compared to untreated cells.

FIG. 8

FACS profile of H1299 cells treated with the delta receptor antagonist Naltrindole and TNF, showing cell cycle (G2/M) arrest prior to apoptosis.

FIG. 9a

Quantitative representation of FACS analysis of (p53 null) H1299 human lung carcinoma cells treated with haloperidol and TNF showing synergistic apoptotic effect.

FIG. 9b

Quantitative representation of FACS analysis of 293 cells showing synergistic cooperation between haloperidol and the NF-κB subunit p65(RelA) in inducing apoptosis.

FIG. 9c

Quantitative representation of FACS analysis of 293 cells showing that apoptosis induced by haloperidol, a sigma receptor ligand, is dependent on NF-κB (in these cells which have functionally inactivated p53).

FIG. 10a

Quantitative representation of FACS analysis of p53 null lung carcinoma (H1299) cells showing cooperation between the sigma receptor ligand rimcazole and TNF in inducing apoptosis.

FIG. 10b

Quantitative representation of FACS analysis of H1299 cells showing cooperation between the sigma receptor ligand rimcazole and the kappa receptor agonist trans-U50488 in the induction of apoptosis.

FIG. 11a

Quantitative representation of FACS analysis of L428 (Hodgkins lymphoma) cells showing apoptosis induction by haloperidol at 0.1 mM, 0.01 mM and 0.001 mM.

FIG. 11b

Quantitative representation of FACS analysis of L428 (Hodgkins lymphoma) cells showing apoptosis induction by rimcazole at 0.1 mM, 0.01 mM and 0.001 mM.

FIG. 11c

Quantitative representation of FACS analysis of control B lymphoid (Daudi) cell line which are unaffected by rimcazole at 0.1 mM, 0.01 mM and 0.001 mM.

FIG. 12

Quantitative representation of FACS analysis of hormone responsive (MCF7) and hormone unresponsive (MDA MB 231) human breast carcinoma cells showing a greater propensity of rimcazole to induce apoptosis and cell division cycle arrest in the hormone unresponsive (advanced stage) breast cancer cells.

FIG. 13

FACS analysis of hormone insensitive (advanced) breast cancer (MDA MB 468) cells showing apoptosis induction by rimcazole alone, and synergistic apoptosis induction when two sigma ligands are combined: rimcazole and cis-U50488.

FIG. 14a

Phase micrographs of MCF 7 breast cancer cells expressing a conditional mutant form of p53 which is inactive at the restrictive temperature of 37 degC (upper panels) but is activated if the temperature of the culture is reduced to 32 degC (lower panels); rimcazole at concentrations of 0.01 mM and below induces apoptosis to a substantially greater extent when p53 is activated in these cells by temperature reduction.

FIG. 14b

Quantitative representation of FACS analysis of human osteosarcoma (Saos-2::p53$^{teti}$) cells treated with low dose rimcazole and the tetracycline analogue doxycycline (to induce stably transfected p53 driven by a tetracycline inducible promoter); this shows synergistic apoptosis induction when the two agents are combined.

FIG. 14c

Quantitative representation of FACS analysis of 293 cells transiently transfected with p53 cDNA and treated with rimcazole; this illustrates synergistic apoptosis induction when the two treatments are combined.

FIG. 15

Shows the results of xenograft studies using the MDA MB 468 human breast carcinoma cell line in mice in the presence or absence of the sigma receptor ligands rimcazole, cis-U50488 and haloperidol. FIG. 15a shows mean tumour volume versus time; FIG. 15b shows mean excised tumour weights and FIG. 15c shows mean excised tumour weights for selected tumours. All show some reduction of tumour growth in the presence of the sigma ligands, especially rimcazole.

The experiments described in the examples were performed using methods well-known to those skilled in the art and documented in standard text books in the field (e.g. Chapters 4 and 5, Methods in Cell Biology Vol 46 editors L. M. Schwartz and B. A. Osborne, Academic Press Ltd, London 1995 provides inter alia details on detection of apoptosis and cell division cycle arrest by FACS).

The apoptotic effect of TNF is known to be offset by NF-κB activation (Beg and Baltimore 1996 Science Vol. 274 pp 783-784; Wang et al. 1996 Science Vol. 274 pp 784-787; Van Antwerp et al 1996 Science Vol. 274 pp 787-789). In this experiment we addressed whether opioid-like agents would enhance the apoptotic effect of TNF.

1.1 Opioid Receptor Ligands Enhance Tumour Necrosis Factor (TNF)—Induced Death by Provision of a 'Pro Apoptotic Switch to Activated NF-κB FIG. 1 shows a quantitative representation of FACS analysis of 293 cells (transformed kidney epithelial cells) using the nucleic acid dye, propidium iodide; this gives a measure of DNA content in the cell. This technique allows a simultaneous assessment of the cell division cycle profile of cells as well as the presence of apoptotic cells. Viable cells (as a percentage of the total cell population) in G1/S or G2/M phase of the cell cycle are represented as stippled or horizontal-hatched bars. Apoptotic cells have a reduced DNA content due to endonuclease activation which occurs during execution of the apoptotic programme; apoptotic cells (as a percentage of the total cell population) are depicted as a sub-G1 population (diagonal-hatched bars). Untreated or TNF-treated cells (FIGS. 1 and 2) have very low levels of apoptosis (2-4%). Treatment of cells with Naltrindole induces 46% of cells to become apoptotic at this time point (approximately 48 hours after treatment addition); when naltrindole and TNF are combined, there is a marked increase in apoptosis to 86%, which is reduced to 15% in the presence of a repressor of NF-κB activity (IκB).

Prevailing scientific opinion would indicate that the most obvious explanation for cooperation between opioid receptor ligands and TNF is that naltrindole is inhibiting NF-κB activation. We were therefore surprised to find that when a dominant inhibitor of NF-κB activation, a non-degradable form of IκB, was transfected into cells, the apoptotic peak was markedly reduced and there was reappearance of G1 viable cells, indicating that death was largely abrogated (FIGS. 1a and b). The few remaining dead cells were likely to reflect the non-transfected population since it is rare to achieve 100% transient transfection efficiency. These data therefore indicate that in this cell system (which is functionally p53 null) the cooperation between naltrindole and TNF requires NF-κB activation. Data from other laboratories has shown that TNF activates an NF-κB mediated drive to survive which is inhibited by IκB. Inhibition of NF-κB blocks the cooperativity between opioids and a non-lethal dose of TNF. We therefore propose that opioid pathways provide a pro-apoptotic switch to activated NF-κB which may be operating in one of the following ways:

1. Opioids selectively inhibit the anti-apoptotic arm of NF-κB activity but spare its pro-apoptotic effects; in this way balance is shifted towards death. In non-transformed cells, abrogation of a single survival pathway would not be expected to cause the death of a cell. In tumour cells, an acquired preferential dependence on NF-κB-mediated survival would render the tumour cell preferentially susceptible. Opioids are not providing a global inhibition of NF-κB activation since transfection of IκB alone has no effect on viability.

2. Opioids selectively promote the pro-apoptotic mediators downstream from NF-κB; in this way, the balance would be shifted towards death and again, we would anticipate that tumour cells would be preferentially affected due to the tumour cell being poised on a knife-edge between life and death, for the reasons discussed previously.

3. A combination of the above.

4. Any of the mechanisms described in 1-3, which are reliant on NF-κB activation, may be implemented by an indirect effect of opioids on heterologous transcription factors; a number of these cooperate with NF-κB and play an important role in specifying NF-κB-responsive gene targets (Perkins, 1997, Int. J. Biochem. Cell Biol. Vol. 29 pp 1433-1448).

It is interesting that a non-lethal dose of TNF (i.e. one which has no apoptotic effect on its own) cooperates powerfully with opioid-like receptor ligands and this would not have been anticipated. At this dose of TNF we propose that an NF-κB-mediated anti-apoptotic drive outweighs its death agonistic effects. The use of a very low dose of TNF makes the combination with opioids a particularly attractive therapeutic possibility as the known harmful side effects of TNF will be greatly reduced. The cooperation with TNF is seen with all opioid-like compounds which induce apoptosis: these include naltrindole, trans-U50488, noscapine and sigma receptor ligands including haloperidol and rimcazole.

1.2 Secretory Proenkephalin Cooperates with TNF in Apoptosis Induction

In Section 1.1, a cooperative effect was observed between TNF and naltrindole in inducing apoptosis. Because IκB abolished this apoptotic induction, NF-κB was implicated in this apoptotic induction pathway.

In WO96/06863 it was shown that cytoplasmic and secretory proenkephalin repress apoptosis in at least some cell types. Here we show that secretory proenkephalin can also act to promote apoptosis in concert with TNF. Importantly, we also show that the cooperation between secreted proenkephalin and TNF is prevented by inhibition of NF-κB activation, using IκB.

FIG. 2 provides a quantitative representation of FACS profiles from 293 cells treated for 48 hours with a non-lethal concentration of TNF (5 ng/ml) or transiently transfected with 5 μg of plasmid DNA encoding proenkephalin destined for the secretory pathway; in both cases no induction of apoptosis is observed. However, when proenkephalin is overexpressed in combination with TNF (bars as shown) there is a marked increase in the percentage of apoptotic (sub-G1) cells diagonal-hatched bars and a concomitant reduction in viable cells (stippled and horizontal-hatched bars). The cooperation between proenkephalin and TNF is inhibited by co-transfection of 5 μg of plasmid DNA encoding the NF-κB inhibitor, IκB (bars on extreme right of graph) there is a recovery in the viable cells with a greater than 50% reduction in the percentage of sub-G1 (apoptotic) cells. Notably, IκB alone does not induce death; this indicates that opioids are not inducing apoptosis by providing a "global" inhibition of NF-κB activation but instead, are switching NF-κB into an apoptotic mode.

The ability of secretory proenkephalin to cooperate with TNF in an NF-κB dependent manner to induce death in 293 (transformed human kidney) cells is therefore analogous to that seen with opioid-like compounds.

1.3 Opioid-Like Receptor Ligands Cooperate with TNF to Induce Apoptosis in Human Cancer Cells In Sections 1.1 and 1.2, we have shown a cooperative effect between TNF and an opioid-like receptor ligand and between TNF and proenkephalin.

The cooperation between opioid-like receptor ligands and TNF is evident in all human cancer cell lines we have tested so far including lung and colon cancer. Here we show (FIG. 3) the effect of 48 hours treatment with the natural opium alkaloid noscapine at $10^{-4}$M on p53 null lung cancer (H1299) cells; 39% of cells are apoptotic but there are still many viable cells. However, when noscapine is combined with TNF at 5 ng/ml (which on its own has no effect on cell viability) there is a marked reduction in viable cells and a marked increase in apoptotic cells (to 74% of the total cell population) Importantly, H1299 cells lack functional p53 protein and therefore the cooperation with TNF does not require p53, which would be consistent with dependence on NF-κB.

FIG. 4 illustrates apoptotic death induced by noscapine and TNF in human colon cancer (HT29) cells. In this particular cancer cell type, noscapine on its own at $10^{-4}$M induces apoptosis in 67% of the cell population; there is an additional increase when TNF is added.

The cooperative effect of opioid-like ligands and TNF on the NF-κB dependent induction of apoptosis has been shown for different ligands on different tumour cell lines. This cooperation between opioids and TNF, which is dependent on NF-κB, indicates that other anti-tumour therapies which are associated with NF-κB activation such as ionising radiation, nocodazole, etoposide, and daunorubicin will be enhanced by opioids.

1.4 Opioids and Proenkephalin (Nuclear and Secretory) Cooperate with the RelA(p65) Subunit of NF-κB to Induce Death In the previous examples, opioid-like agents were shown to switch NF-κB that had been activated by TNF into a pro-apoptotic activity. The interaction between proenkephalin and NF-κB was investigated further in this example.

NF-κB is composed of subunits in different dimeric combinations. The RelA(p65) subunit of NF-κB is dysregulated in inflammatory diseases such as arthritis, and is downregulated on successful treatment (Handel et al. 1995 Arthritis and Rheumatism Vol 38, pp 1762-1770; Marok et al. 1996 Arthritis and Rheumatism Vol 39 pp 583-591; Tsao et al. 1997 Clinical Immunology and Immunopathology Vol. 83 pp 173-178); RelA(p65) is also dysregulated in atherosclerosis, a disease characterised by features of chronic inflammatory processes (Brand et al. 1996 Journal of Clinical Investigation Vol 97 pp 1715-1722; Bourcier et al. 1997 Journal of Biological Chemistry Vol. 272 pp 15817-15824); abnormal expression of RelA(p65) also occurs in Alzheimer's disease (Terai et al. 1996 Brain Research Vol 735 pp 159-168; Kitamura et al. 1997 Neuroscience Letts Vol 237 pp 17-20) Dysregulation of RelA(p65) would be generally expected to provide an anti-apoptotic drive (Beg et al., 1995 Nature Vol 376 pp 167-170). NF-κB is also constitutively activated (RelA (p65) is translocated to the nucleus) in at least some tumours such as Hodgkins lymphoma and late stage breast cancer. We therefore determined whether proenkephalin and opioids would provide a pro-apoptotic switch to overexpressed RelA (p65), as an experimental model of diseases where RelA(p65) is dysregulated. If so, this would allow us to predict that opioids would terminate or at least attenuate the inflammatory processes which are central to many major diseases-.

In this example we show that overexpressed nuclear and secretory proenkephalin cooperate with overexpressed RelA (p65) to induce apoptosis. FIG. 5 shows a series of phase micrographs of 293 cells transiently transfected with DNA encoding nuclear proenkephalin (PE) on its own (top left), in combination with the RelA(p65) subunit of NF-κB (top right), and in triple combination with RelA(p65) and p53 (bottom right). Nuclear proenkephalin (PE) in combination with overexpressed RelA(p65) (NF-κB)produces dead, shrunken apoptotic cells (top right panel); in contrast, proenkephalin, or NF-κB alone (left hand panels) shows no significant death. This Figure also illustrates the more marked effect when a triple combination of proenkephalin, RelA(p65) and p53 is used which exemplifies the potential of combination approaches using opioids together with activators of both NF-κB and p53; it also suggests that opioids have the potential to override the reciprocity between NF-κB and p53 (Neil Perkins, unpublished). Secretory proenkephalin and opioid-like compounds also cooperate with RelA(p65) in apoptotic induction (see example below for haloperidol).

In the context of anti-tumour therapy, the ability of opioids to cooperate with the RelA(p65) subunit of NF-KB indicates that opioids will cooperate generally with activators of NF-κB which will include compounds which were hitherto alien to the arena of tumour therapy; in particular, we propose that microtubule depolymerising agents (such as nocodazole, colchicine, podophyllotoxin, vinblastine), which activate NF-κB as a consequence of this, would offer powerful combinatorial possibilities. The ability of opioids to cooperate generally with activators of NF-κB also demonstrates the potential for cooperation with inflammatory mediators and cytokines such as lipopolysaccharide, lymphotoxin-α, interferon-g; also anti-CD40 antibodies, CD40 ligand etc (see table above; from Siebenlist et al 1994 Annu Rev Cell Biol Vol. 10 pp 405-455), using the agents at low doses to minimise pro-inflammatory or other harmful side effects. Importantly, some of these agents (such as CD40 ligand) activate NF-κB in a cell type specific manner and so would target anti-tumour effects to the cell type in which the malignancy has arisen such as lymphoid cells.

2. Death Induced by Opioid Receptor Ligands is Itself Partly Dependent on NF-κB Activation Examples 1.1-1.4 indicated that opioids had the ability to provide a "pro-apoptotic switch" to NF-κB activated by agents such as TNF. This finding led us to address whether opioids may themselves activate NF-κB or induce a pro-apoptotic switch to constitutively activated NF-κB in tumour cells, leading to death. The following examples demonstrate that all the opioid-like compounds tested which induce apoptosis (including naltrindole, trans-U50488, noscapine, and sigma ligands such as haloperidol) are indeed at least partly dependent on NF-KB activation for their effect.

FIG. 6 depicts percentages of apoptotic compared with viable 293 (transformed human kidney) cells following treatment for 48 hours with naltrindole or trans-U50488 (middle left); in both cases there is a marked induction of sub-G1 (apoptotic) cells and a marked reduction in viable cells; in contrast, opioid treatment of cells transfected with mutant "super-repressor" IκB, to prevent NF-κB activation, fails to induce death. It is important to note that this apparent complete protection from death does not indicate exclusive dependence on NF-κB since the p53 pathway is functionally inactivated in these cells by the adenoviral gene products E1B 19K and 55K. However, the lack of reliance on p53 for the induction of death by opioids makes p53 null cancer cells a particularly attractive target for apoptosis induction according to the various aspects of this invention, since these cells are more resistant to anti-tumour therapies such as ionising radiation and DNA damaging drugs. Apoptosis is therefore induced at least partly through an NF-κB mediated pathway.

The ability of other activators of NF-κB such as TNF to enhance the death effect of opioids indicates that opioid activation of NF-κB is not saturating. However, since there is a dearth of data on the state of NF-κB activation in tumour cells, we cannot at this stage confidently distinguish whether opioids are themselves activators of NF-κB or are switching pre-existing activated NF-κB into an apoptotic mode; however, the outcome would be the same.

These examples show that opioid-like compounds achieve their apoptotic effect through an NF-κB dependent mechanism. This is shown, in the present application, for several different classes of opioid-like compound (including naltrindole, trans-U50488, noscapine and sigma ligands such as haloperidol).

3. Tumour Cells in which NF-κB is Constitutively Activated at High Levels, such as Hodgkins Lymphoma Cells, are Particularly Susceptible to the Effects of Opioids; Control Lymphoid Cell Lines are Unaffected.

Because opioid-like compounds achieve apoptotic induction through NF-κB, as shown in the previous examples, they may be particularly suitable for certain therapeutic applications.

Few studies have addressed how widely NF-κB is dysregulated in tumour cells. However, there are some tumour types where NF-κB has been shown to be constitutively activated; for example, in Hodgkins lymphoma cells NF-κB is deregulated at high levels and fails to respond to activators of NF-κB such as CD40 ligand (Wood et al. 1998 Oncogene Vol. 16 pp 2131-2139). We therefore addressed whether Hodgkins cells would be more susceptible to the effects of opioid-like agents, in the absence of concomitant activators of NF-κB.

FIG. 7a illustrates a FACS profile of L428 Hodgkins lymphoma cells treated for 48 hours with either noscapine or naltrindole. Both agents at $10^{-4}$M induce the majority of the cell population to apoptose; even at $10^{-5}$M a substantial amount of apoptosis is seen and there is in addition evidence of mitotic arrest (increase in percentage of G2/M cells). Thus, Hodgkins lymphoma cells are particularly susceptible to the effects of opioids; the degree of death induction in Hodgkins cells by opioid-like receptor ligands administered alone, is approximately the same as that induced by opioids in combination with TNF in other cancer cell lines (see for example lung cancer cells treated with noscapine at $10^{-4}$M in the present and absence of TNF, FIG. 3). These data therefore indicate that opioid-like compounds can confer a pro-apoptotic switch to pre-existing activated NF-κB even when it is deregulated at high levels. They also demonstrate comparable activity of naltrindole and noscapine.

FIG. 7b illustrates of control B lymphoid cells, which lack deregulated RelA(p65), treated for 48 hours with noscapine or naltrindole. Interestingly, untreated control B cells have a high level (approximately 50% of cells) of basal apoptosis (sub-G1) which reflects "appropriate" apoptosis; this "appropriate" apoptosis is absent in untreated Hodgkins lymphoma cells (FIG. 7a) which indicates less reliance on external factors. Many haemopoietic cell lines are extremely sensitive to their supply of external survival signals and readily undergo apoptosis in tissue culture as they are in an alien environment. It is noteworthy that neither noscapine nor naltrindole affect this "appropriate" apoptosis (approximately 50% cells remain apoptotic); also, the proportion of viable, cycling cells is very similar to that in untreated cell populations. These data therefore provide powerful evidence that opioid-like compounds spare proliferating non-tumour cell populations in both cell division cycle arrest and apoptotic effects.

These results demonstrate the preferential effect of opioid-like compounds on tumour cells compared to non-tumour cells.

4. Evidence for Induction of Mitotic Arrest Prior to Apoptosis by Opioid-Like Compounds.

The idea that apoptosis is an aborted mitosis is not generally accepted, as discussed above; it is certainly not a common mechanism of apoptosis induction. However, we have noted that when tumour cells are induced to apoptose in response to all the opioid-like compounds we have tested, this is preceded by an induction of cell division cycle arrest; this is also a feature of cells treated with sub-apoptotic doses of opioids when combined with TNF (see for example haloperidol plus TNF, FIG. 9a). Induction of mitotic arrest and apoptosis by noscapine has also been described by Ye et al (1998 PNAS, see above).

FIG. 8 depicts a FACS scan of H1299 cells treated with naltrindole which shows a marked induction of apoptosis after 36 hours (bottom panels); however, 12 hours earlier (at 24 hours), this was preceded by the appearance of a G2/M peak (middle panels) which indicates the possibility of mitotic arrest preceding entry into apoptosis. However, the simultaneous demonstration of at least a proportion of cells in apoptosis at this same time point suggests that this may not be an exclusive mechanism of apoptosis induction by opioids.

Nonetheless, it is an otherwise uncommon profile which as far as we can tell is shared by all pro-apoptotic opioid-like compounds. The advantage of this combination of mitotic arrest and apoptosis indicates a back-up mechanism if apoptosis fails; furthermore, as shown in the preceding section, proliferating non-Hodgkins cells do not arrest in mitosis which indicates further cell cycle-mediated potential for preferential effects on tumour compared to non-tumour cells.

This example shows the link between opioid induced apoptosis and mitotic arrest.

It is important however to emphasise that induction of mitotic arrest by opioids themselves is not a pre-requisite for apoptosis induction; indeed, WO96/06863 described a powerful combinatorial effect between nocodazole, which arrests cell in mitosis, and opioids. As described above, nocodazole depolymerises microtubules and in so doing, activates NF-κB; the role of opioids in this case is likely to be the provision of a pro-apoptotic switch to NF-κB activated through the microtubule-destabilising effect of nocodazole. It is important however to emphasise that the combination of microtubule depolymerising agents with opioids could not have been predicted as a general combinatorial mechanism at the time WO96/06863 was filed; this is because NF-κB activated as a consequence of microtubule depolymerisation would be generally surmised to limit any apoptotic effect.

A summary therefore of possible ways in which opioids cooperate with NF-κB in the induction of death, which are not mutually exclusive and may even act in cooperation, would be as follows:

1. Opioid-like receptor ligands become translocated to the cell interior through binding to cell surface molecules, and are thence delivered to microtubules where a depolymerising effect induces mitotic arrest and also activates NF-κB. Opioid-like agonists or antagonists then modulate the outcome of NF-KB activation by providing a pro-apoptotic switch in the way described.

2. Other agents which depolymerise microtubules such as nocodazole (and which may possibly synergise with opioid effects mediated through different binding sites on tubulin) activate NF-κB which is then converted into apoptotic mode by opioids.

3. Opioid-like agents provide a pro-apoptotic switch to NF-κB activated by agents which act independently of microtubules, of which there are many: TNF is one example and the cooperation of opioids with RelA(p65) exemplified the potential of multiple NF-κB activators.

4. Opioid-like agents themselves may activate NF-κB independently of microtubules, through signal transduction events mediated at the cell surface or by binding to intracellular opioid receptors such as have been reported in the cell nucleus (Ventura et al. 1998 J. Biol. Chem. Vol 273 pp 13383-13386); these events would lead to phosphorylation-mediated degradation of the inhibitor protein IκB and translocation of p65RelA (NF-κB) to the cell nucleus (Verma et al 1995 Genes Dev. Vol. 9 pp 2723-2734). Opioid-like agents would in turn modulate the outcome of NF-κB activation to end in an apoptotic fate.

5. Sigma Receptor Ligands, Haloperidol and Rimcazole, are Powerful Inducers of Apoptosis in Tumour Cells and Employ the Same Mechanism as Other Opioid-Like Agents.

We then determined whether sigma receptor ligands would induce apoptosis in tumour cells, by the same mechanism as the other opioid-like receptor ligands. In these examples, we show that ligands which have antagonistic effects at the sigma receptors, haloperidol and rimcazole, are potent inducers of NF-κB dependent apoptosis in all tumour cells we have tested so far. These data suggest that a sigma-like receptor mediates a survival advantage on which tumour cells have come to preferentially depend.

As shown herein, in Example 7, other sigma receptor types mediate death rather than survival. Agonistic ligands for these sigma receptor types would also be pro-apoptotic.

FIG. 9a illustrates cooperativity between haloperidol and TNF in the induction of apoptosis in p53 null human lung cancer cells; this cooperativity is particularly marked at the $10^{-5}$M dose level of haloperidol (4% apoptosis is converted to 59% apoptosis when the two agents are combined).

FIG. 9b demonstrates that haloperidol also cooperates powerfully with the RelA(p65) subunit of NF-κB. This experiment was carried out in the 293 cell line to achieve high levels of p65 transfection efficiency. There is a powerful cooperation between haloperidol at $10^{-5}$ M combined with RelA(p65) (47% of cells are apoptotic compared with 2-3% apoptosis with either treatment on its own). Thus, a truly synergistic apoptotic effect is revealed by the combination of haloperidol and RelA(p65) (as it is also with haloperidol and TNF).

FIG. 9c demonstrates the dependence of haloperidol-induced death on NF-κB (in 293 cells, where p53 is functionally inactivated); sub-G1 apoptotic cells are markedly reduced (from 58% to 5% of the total cell population) when plasmid DNA encoding non-degradable mutant IκB is transfected prior to haloperidol treatment.

Rimcazole, another more specific sigma receptor antagonist which lacks the dopamine antagonist effects of haloperidol, produces the same effects. Interestingly, both haloperidol and rimcazole cooperate with trans U50488.

FIG. 10a shows cooperativity between a sublethal dose of TNF (tumour necrosis factor) and a sublethal dose of rimcazole (lower left hand panel) to produce significant apoptosis (increasing from 4% to 61% of cells) and a marked reduction in viable cells.

FIG. 10b depicts cooperativity between a sublethal dose of the trans-isomer of U50488 (0.1 mM; sublethal at high cell density—see WO96/06863); and a sublethal dose of rimcazole (0.01 mM); these agents in combination produce significant apoptosis (4-6% apoptosis increasing to 67%). Hence, a kappa opiate receptor ligand synergises with a sigma receptor ligand in apoptosis induction.

These examples show that sigma ligands mediate apoptotic induction through the same NF-κB dependent pathway as other opioid-like agents. Cooperativity with the NF-κB activating agent TNF, inhibition by the NF-κB inhibitor IκB and synergy with the NF-κB subunit RelA(p65} are features of apoptotic induction through this pathway.

Figure 11A:
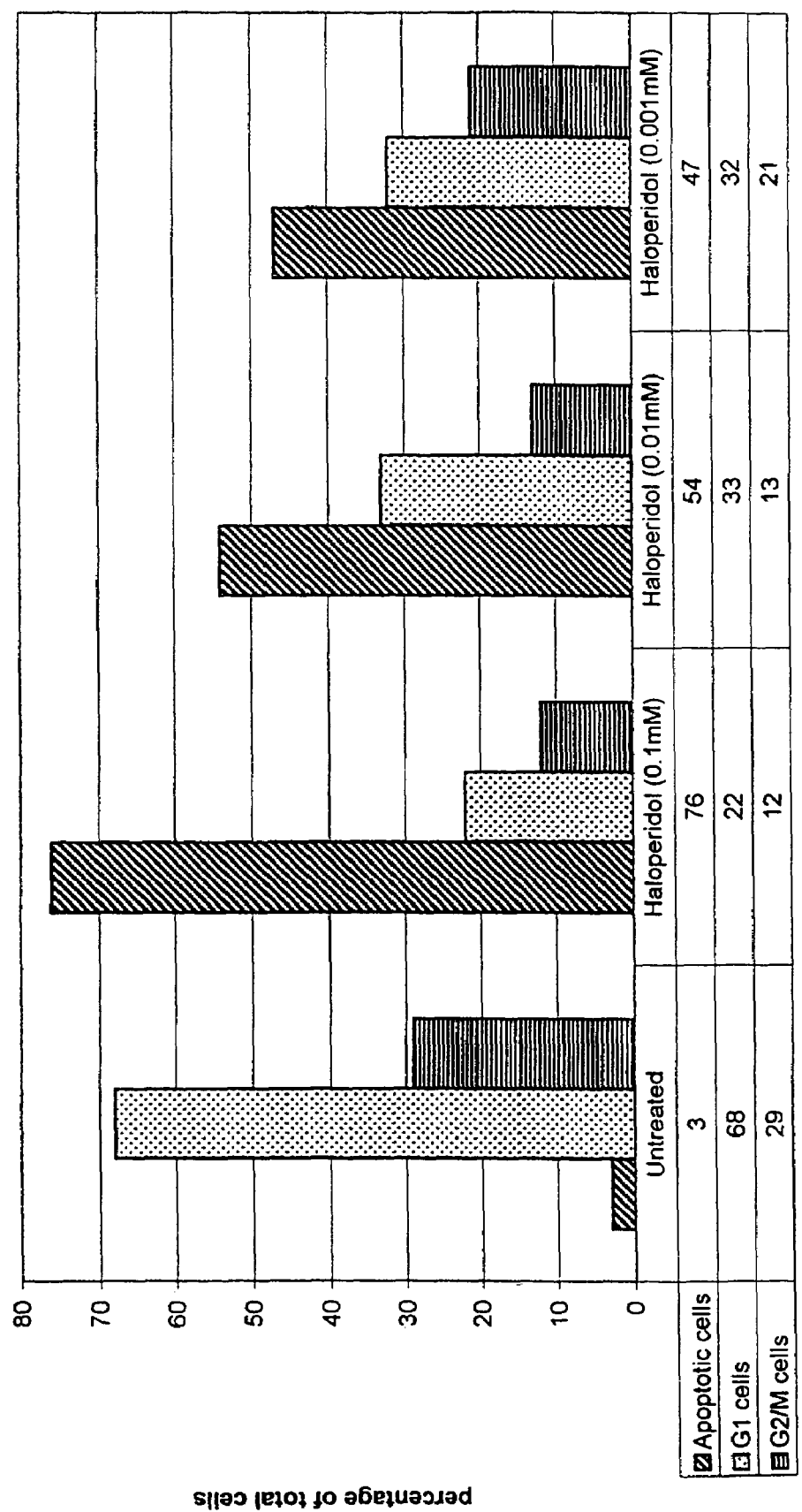
Figure 11B:
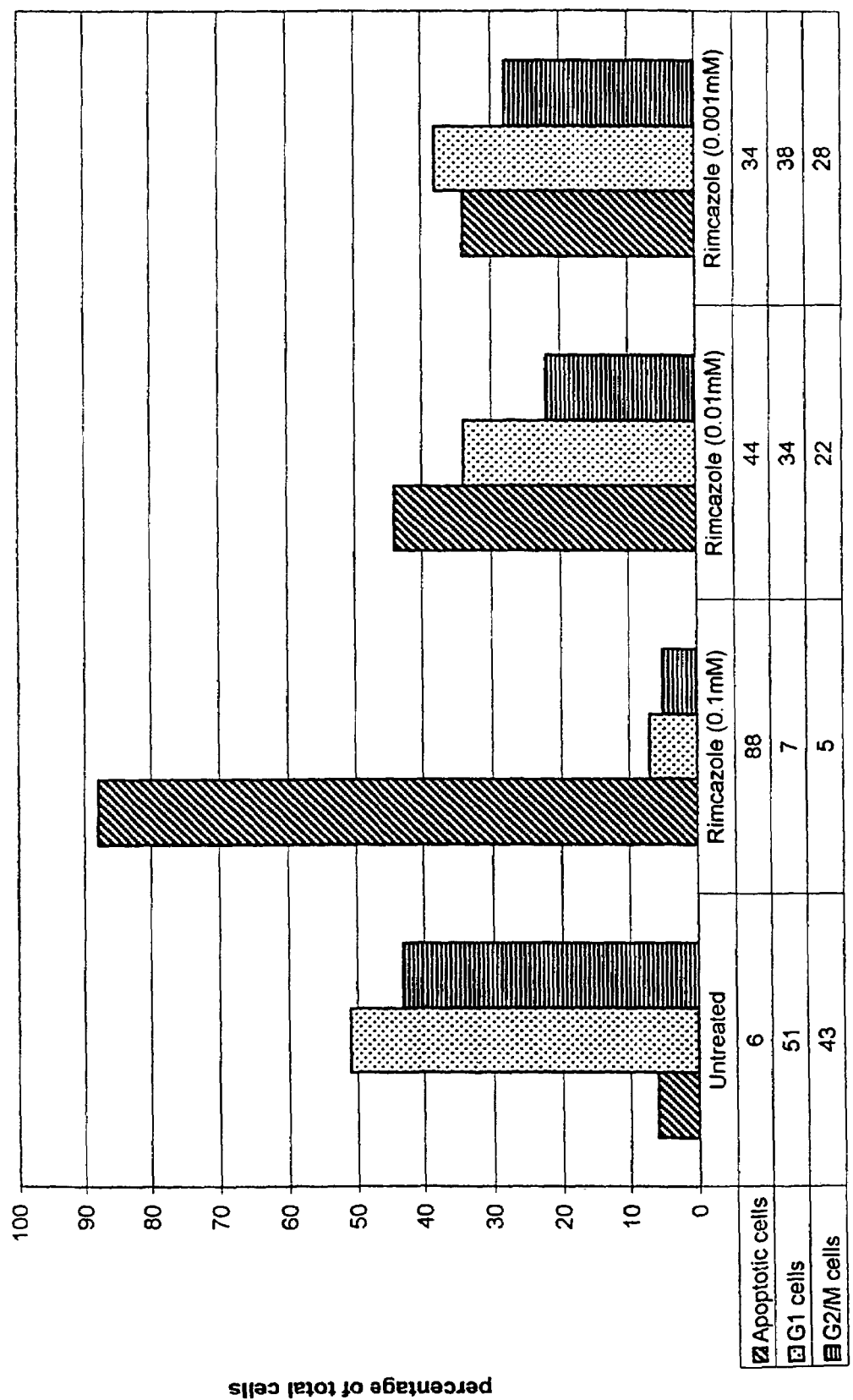

6. Hodgkins Lymphoma Cells, in Which NF-κB is Constitutively Activated at High Levels, have an Increased Sensitivity to the Apoptotic Effects of Sigma Ligands; Control B Cells are Unaffected FIGS. 11a and 11b illustrate a FACS profile of Hodgkins lymphoma cells treated for 22 hours with doses of haloperidol or rimacazole from $10^{-4}$M to $10^{-6}$M. In all cases, there is marked induction of apoptosis (34% to 47% of cells are apoptotic even with micromolar concentrations of compounds). Thus sigma ligands are particularly potent at inducing apoptosis in cells in which RelA(p65) is deregulated.

Figure 11C:
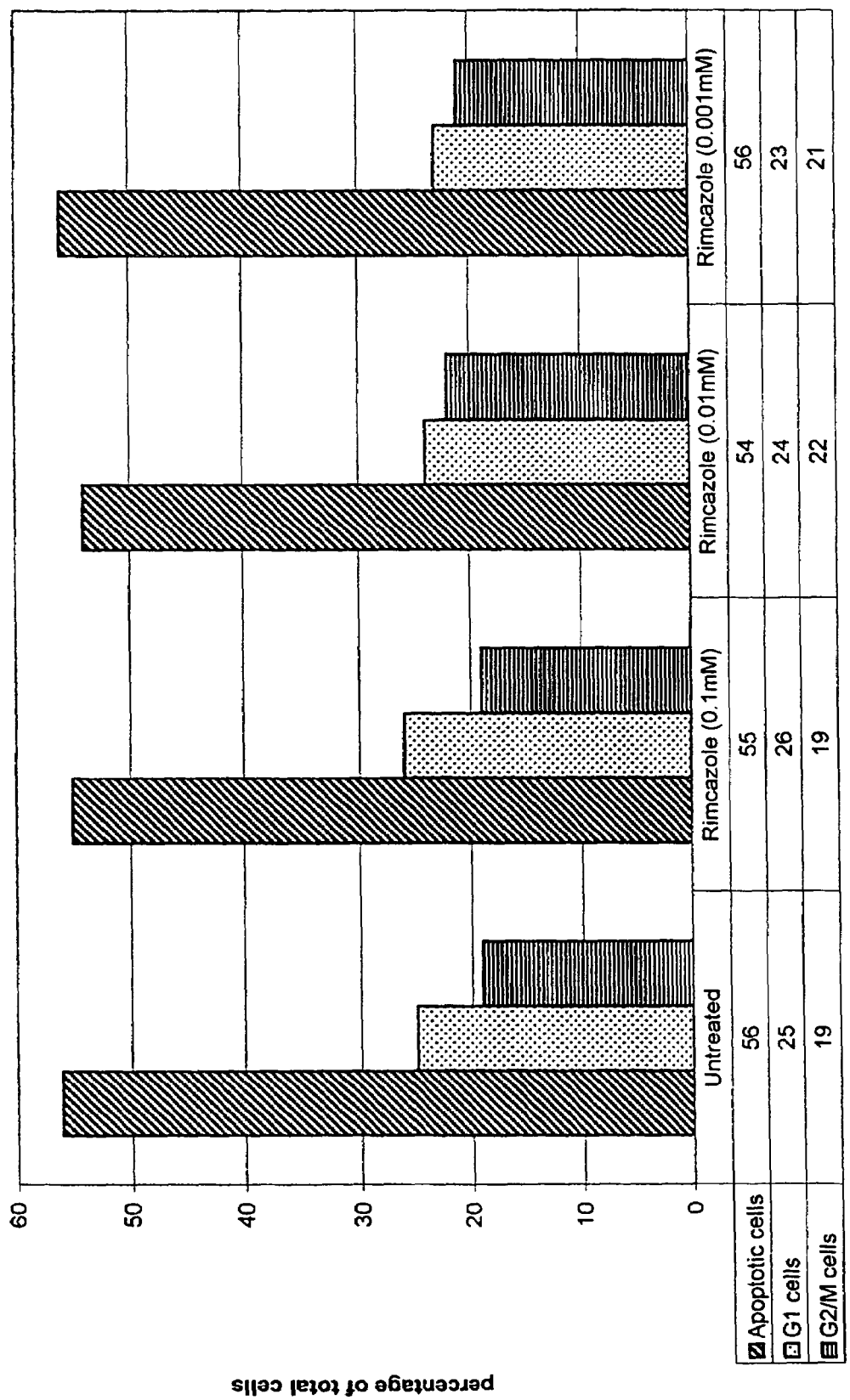

In contrast, FIG. 11c depicts control B cells which lack deregulated RelA(p65) and are unaffected by either rimcazole (FIG. 11c) or haloperidol (not shown). Once again, untreated cells show a significant level of 'appropriate' apoptosis due probably to deprivation of external survival signals; neither rimcazole nor haloperidol affect this 'appropriate' apoptosis. Furthermore, the sigma ligands do not affect the cell cycle profile of the viable control cells. Thus, this is a very clear demonstration of a marked preference of sigma ligands to induce apoptosis in authentic human tumour cells but not in a control population of proliferating cells.

Together, these data provide powerful evidence to support a common mechanism of apoptosis induction which is shared by ligands of classical and non-classical opioid receptors, including the sigma receptor class.

7. Enhanced Sensitivity of Hormone Unresponsive (Advanced Stage) Breast Cancer Cells to Sigma Ligands, Compared to Hormone Responsive Breast Cancer Cells.

Figure 12:
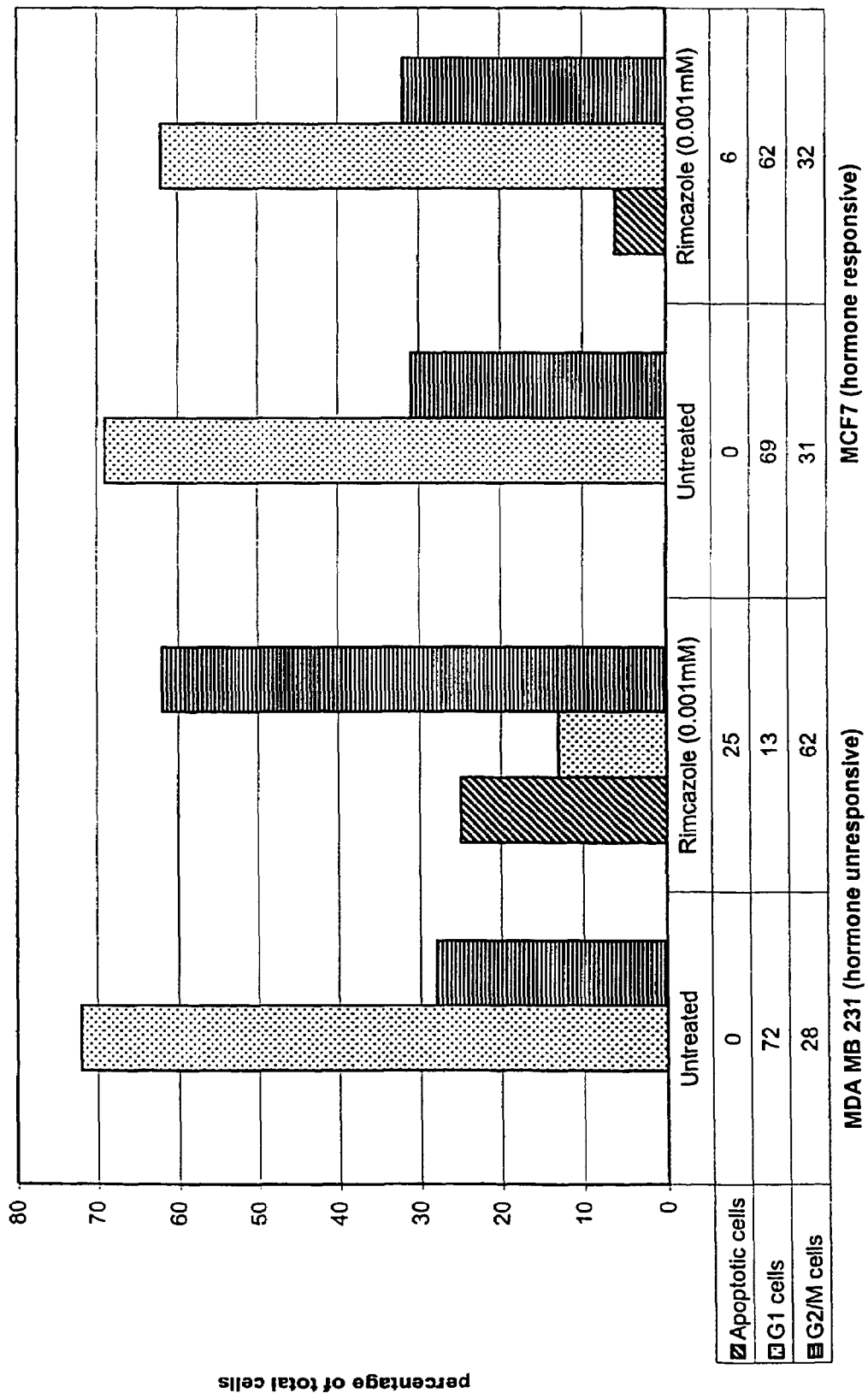

As described above, constitutive activation of NF-κB has been linked to progression of breast cancer to hormone-independent growth (Nakshatri et al. Mol. Cell. Biol. 1997 Vol 17 pp 3629-3639); the cell lines described in this article were MCF 7 (as a model of hormone responsive breast cancer) and MDA (MB) 231 (as a model of hormone unresponsive, advanced, breast cancer). FIG. 12 illustrates substantially greater induction of apoptosis in MDA 231 cells compared to MCF 7 cells with the sigma ligand, rimcazole. In untreated cells of both types, there is negligible apoptosis. However, when treated with rimcazole at 0.001 mM, 25% of the total MDA 231 cell population is apoptotic after 48 hours treatment; this compares with only 6% apoptosis in MCF 7 cells after the same treatment regime and in the same culture conditions. There is also an increase in the proportion of G2/M cells (62% compared to 32% in MCF 7 cells) in rimcazole-treated MDA 231 cells which indicates induction of a G2/M cell division cycle arrest.

Thus, rimcazole induces substantially more apoptosis (25% compared to 6%) and a greater degree of cell division cycle arrest (62% compared to 32%) in hormone unresponsive breast cancer cells compared to hormone responsive breast cancer cells. Sigma ligands may therefore be particularly applicable to advanced stage cancers. In this particular model, a component of enhanced susceptibility may be due to the presence of constitutively activated NF-κB at high levels, which is "switched" into pro-apoptotic mode by the sigma ligand. It also remains possible, as we proposed earlier (page 2 of this document and WO96/06863), that tumour cells progressively acquire a preferential reliance on sigma-mediated survival due to a progressive loss of "back-up" survival mechanisms. This indicates a wider applicability of sigma ligands to advanced cancer even where NF-κB is not implicated.

8. Sigma Ligands Cooperate to Induce Apoptosis in Advanced Breast Cancer Cells.

We propose herein that sigma receptors may mediate death as well as survival; this an unexpected extension of the disclosure of WO96/06863 that opioid-like pathways in general mediate both death and survival and that tumour cells are therefore unduly poised on an opioid-mediated knife edge between life and death.

Figure 13:
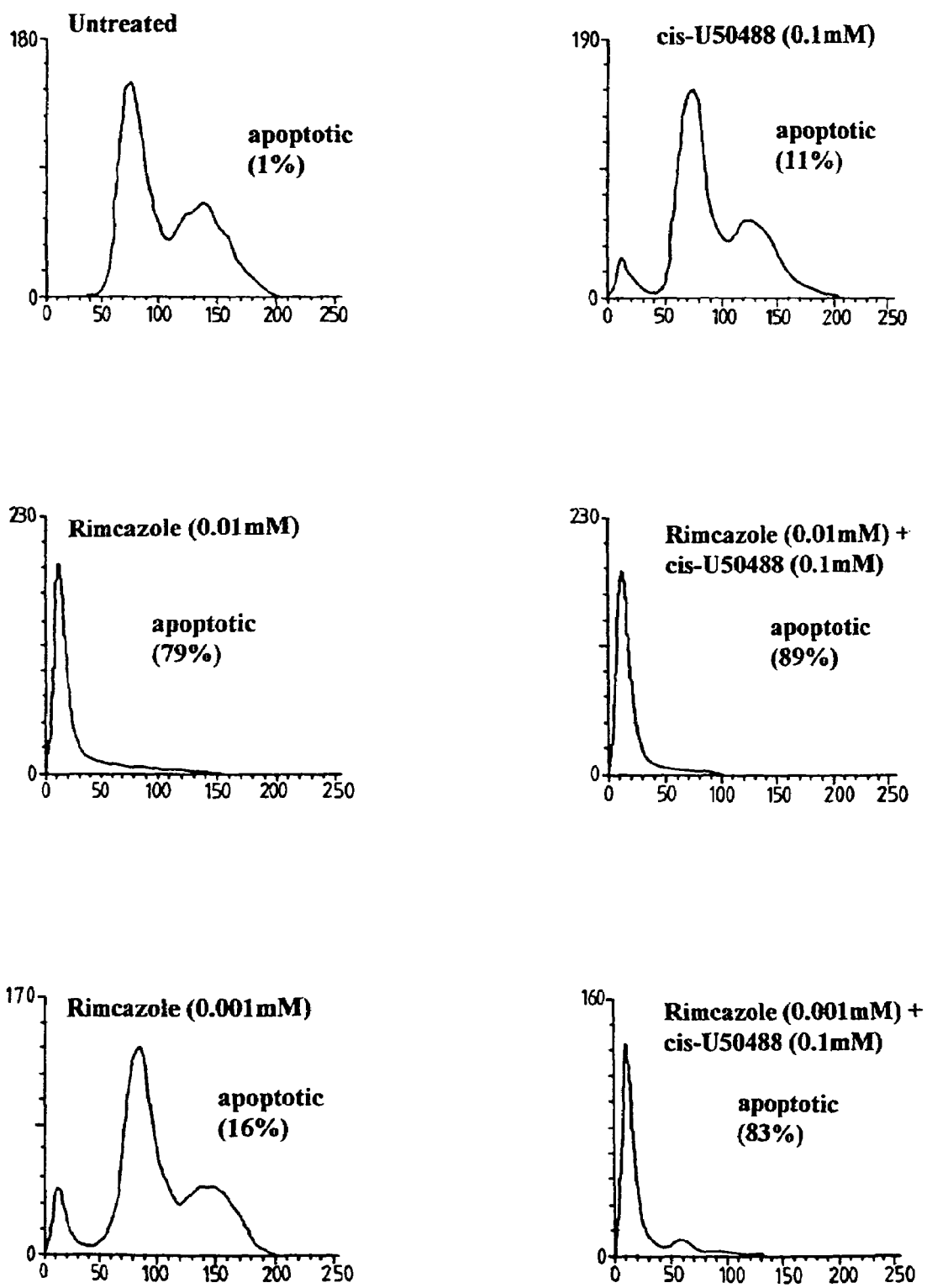

FIG. 13 illustrates a representative experiment in which cooperative induction of apoptosis occurs when two sigma ligands are combined: rimcazole and cis-U50488 (which is distinct from the kappa agonist trans-U50488). In this series of experiments another model of advanced breast cancer was used, MDA (MB) 468, to determine whether sigma ligands would be generally effective against hormone unresponsive breast cancer.

Rimcazole at a concentration of 0.01 millimoles per liter induces apoptosis in 79% of the MDA MB 468 cell population approximately 48 hours after addition of the compound. At a lower concentration of rimcazole (0.001 mM) 16% of cells are apoptotic at the same time point; however, if this is combined with cis-U50488 at 0.1 mM (which on its own induces apoptosis in 11% of the cell population), 83% of the cells are now induced to apoptose; this indicates synergistic death induction when different sigma ligands are combined.

Rimcazole is generally viewed as an antagonistic sigma ligand whereas cis-U50488 is generally viewed as an agonistic sigma ligand. However, it should be stated that, until the signal transduction events which mediate the regulation of apoptosis through the sigma receptor have been defined, the precise categorisation of ligands as either antagonistic or agonistic must remain provisional. That said, these data indicate that more than one sigma receptor (or more than one binding site on the same receptor macromolecule) is involved in regulating apoptosis, and that there is a close functional relationship between these sites.

9. Sigma Ligands Cooperate with p53 in Apoptosis Induction

We propose herein also that sigma ligands could be combined with activators of p53. Many activators of the endogenous p53 pathway (such as etoposide, and ultraviolet and gamma irradiation) induce concomitant activation of the NF-κB pathway. Activation of the p53 pathway causes reduced degradation of the p53 protein which leads to an increase in p53 protein levels within the cell. Therefore, to simulate activation of the p53 pathway in isolation, we used three different model systems in which the p53 protein is conditionally or transiently overexpressed.

Figure 14A:
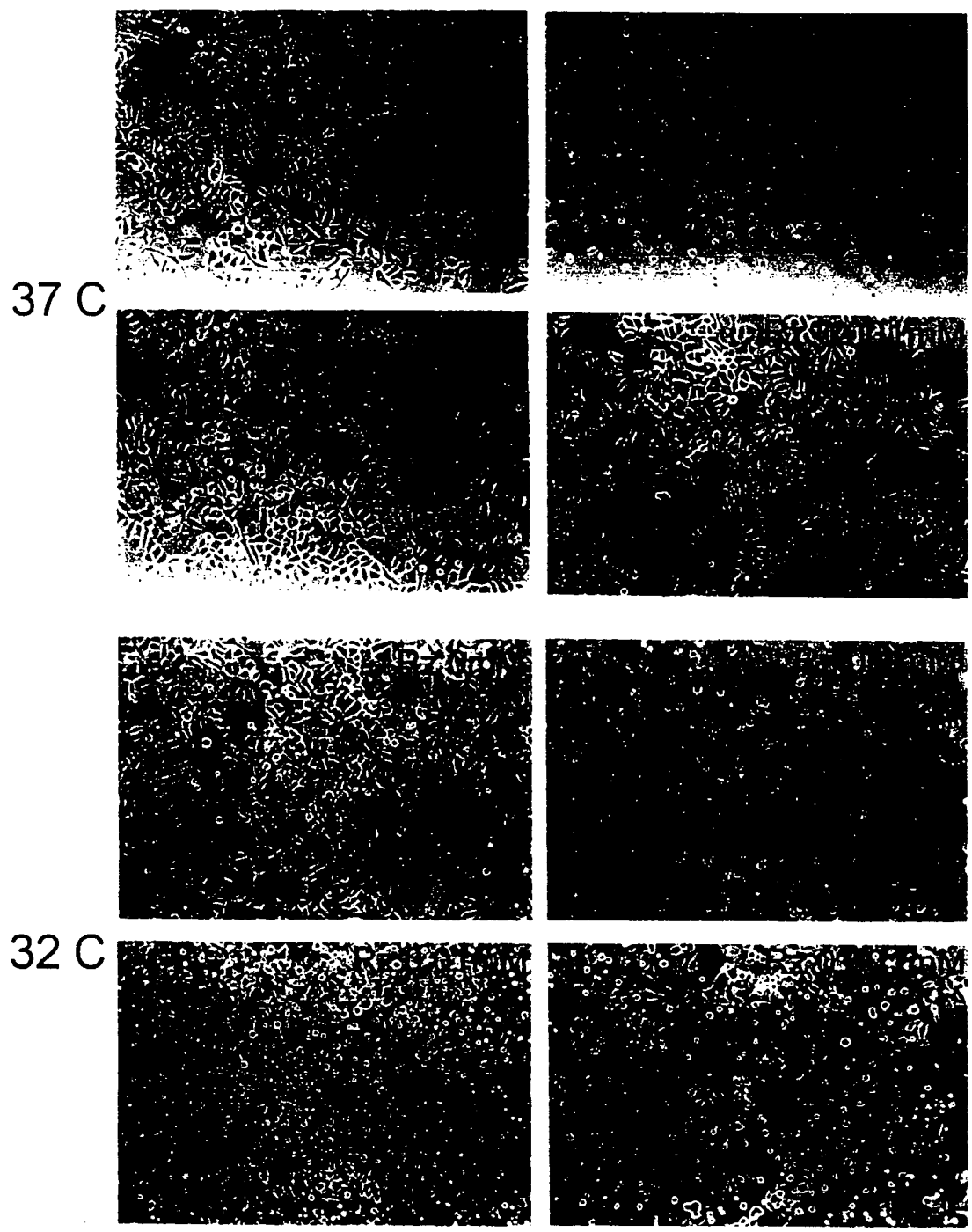

FIG. 14a illustrates breast cancer (MCF 7) cells into which a temperature sensitive mutant form of p53 has been introduced (MCF 7::p53$^{val135}$). When these cells are grown at the permissive temperature (32 degC) p53 adopts a wild-type conformation; but when grown at the restrictive temperature (37 degC) the p53 protein adopts a mutant, inactive conformation.

FIG. 14a (upper 4 panels) illustrate cells grown at 37 degC (at which temperature the p53 protein is largely inactive) in the presence and absence of rimcazole. Apoptosis is induced with rimcazole at high dose (0.1 mM) but the cells are largely unaffected at doses of 0.0 mM and below.

To restore the conformation of the p53 protein to, or closer to, its wild-type state the temperature at which the cells are cultured is reduced to 32 degC; in the absence of rimcazole this has little effect but there is a marked induction of apoptosis (phase micrographs show typically rounded, shrunken cells) with doses of rimcazole which have no effect at the higher temperature (see for example 0.001 mM).

Figure 14B:
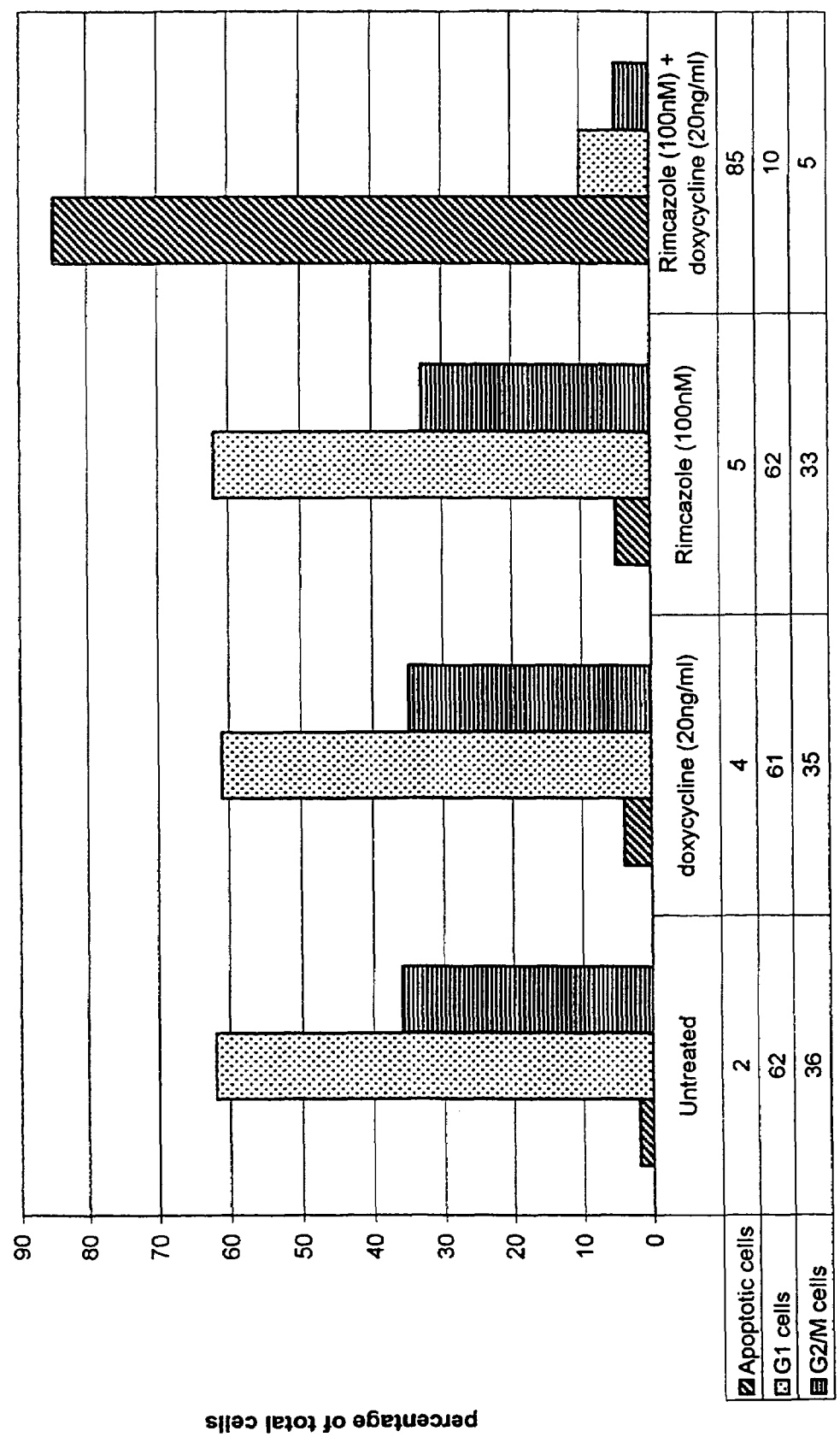

To confirm cooperativity between sigma ligands and the p53 protein, another system in which p53 is under inducible control was used (FIG. 14b). In this model system, (Saos-2::p53$^{teti}$), p53 cDNA driven by a tetracycline-inducible promoter has been introduced into a human osteosarcoma cell line which is ordinarily p53 "null". With increasing doses of the tetracycline analogue, doxycycline, p53 can be induced to progressively higher levels. At high doses of doxycycline, and concomitant high levels of the p53 protein, apoptosis is induced. However, at low doses of doxycycline the small increase in p53 protein levels induces a small percentage of cells (4% of the total population in this representative experiment—FIG. 14b) to undergo apoptosis. Similarly, a low dose of rimcazole (100 nM) induces approximately 5% of the cell population to apoptose. However, when rimcazole at 100 nM is combined with doxycycline treatment at a concentration of 0.02 μg/ml, there is now a synergistic induction of apoptosis such that 85% of cells are apoptotic. In wild-type Saos-2 cells which lack p53 protein, the combination of low dose rimcazole and doxycycline has no effect; this implicates induced p53 as the mediator of cooperativity between rimcazole and doxycycline in Saos-2::p53$^{teti}$ cells.

In FIG. 14c a third model system is illustrated: this illustrates cooperativity between rimcazole and p53 when transiently overexpressed in 293 (transformed human kidney epithelial cells). p53 (at this low dose) and rimcazole alone (at 10 mM concentration) induce only 1% of the cell population to apoptose; however, in combination, there is marked synergy such that 75% of the cell population are now induced to apoptose. Importantly, this also illustrates a biological effect of rimcazole when administered at a low concentration (10 nM) which indicates that authentic sigma receptors are involved in mediating the apoptotic effect.

Together, these data indicate that sigma ligands (or other opioid or opioid-like mediators of apoptosis) could be combined with activators of p53 such as gamma irradiation or genotoxic chemicals in the treatment of tumours which possess wild-type p53 protein; and in combination with gene therapy to reintroduce p53 into tumours which lack functional p53 protein; and in combination with agents which restore p53 conformation to tumours which possess mutant p53 protein.

10. Sigma Ligands Inhibit the Growth of Human Breast Carcinoma Xenografts in Athymic Mice.

Materials and Methods

MDA MB 468 human breast carcinoma cells (described above, Section 7, as a model of hormone-insensitive disease) were grown in tissue culture to 70% confluence, harvested with trypsin:EDTA, washed, resuspended in DMEM and injected subcutaneously bilaterally in the flanks of 60 six-week old female Onu/Onu mice at 2×10$^6$ cells/site.

| Experimental groups | N mice |
| --- | --- |
| 1. Control (water) | 12 |
| 2. Rimcazole (10 mg/kg/day) | 8 |
| 3. Haloperidol (10 mg/kg/day) | 8 |
| 4. cis-U50488 (10 mg/kg/day) | 8 |

All drugs were dissolved in sterile water for injection and frozen as ~2 ml aliquots, except haloperidol which was stored as a powder at RT and made up fresh each day in 45% cyclodextrin. The mice were housed in filter boxes in Maximiser laminar flow cabinets and fed sterilized food and water. All procedures were carried out in class 1 laminar flow hoods using sterile equipment and reagents. The mice were dosed daily by an intraperitoneal route (combined therapies dosed simultaneously) and body weights and tumour measurements recorded at frequent intervals. Tumours were measured with vernier calipers across two perpendicular diameters and results expressed as tumour volume calculated according to the formula $V=4/3\pi[(d1+d2)/4]^3$.

The experiment was terminated on day 45 when tumours were excised, dissected free of surrounding normal tissue and weighed. Differences in growth were compared using the Mann-Whitney U test. Tumour samples were fixed in Methacarn for later histological examination.

Results

Figure 1:
Figure 2:
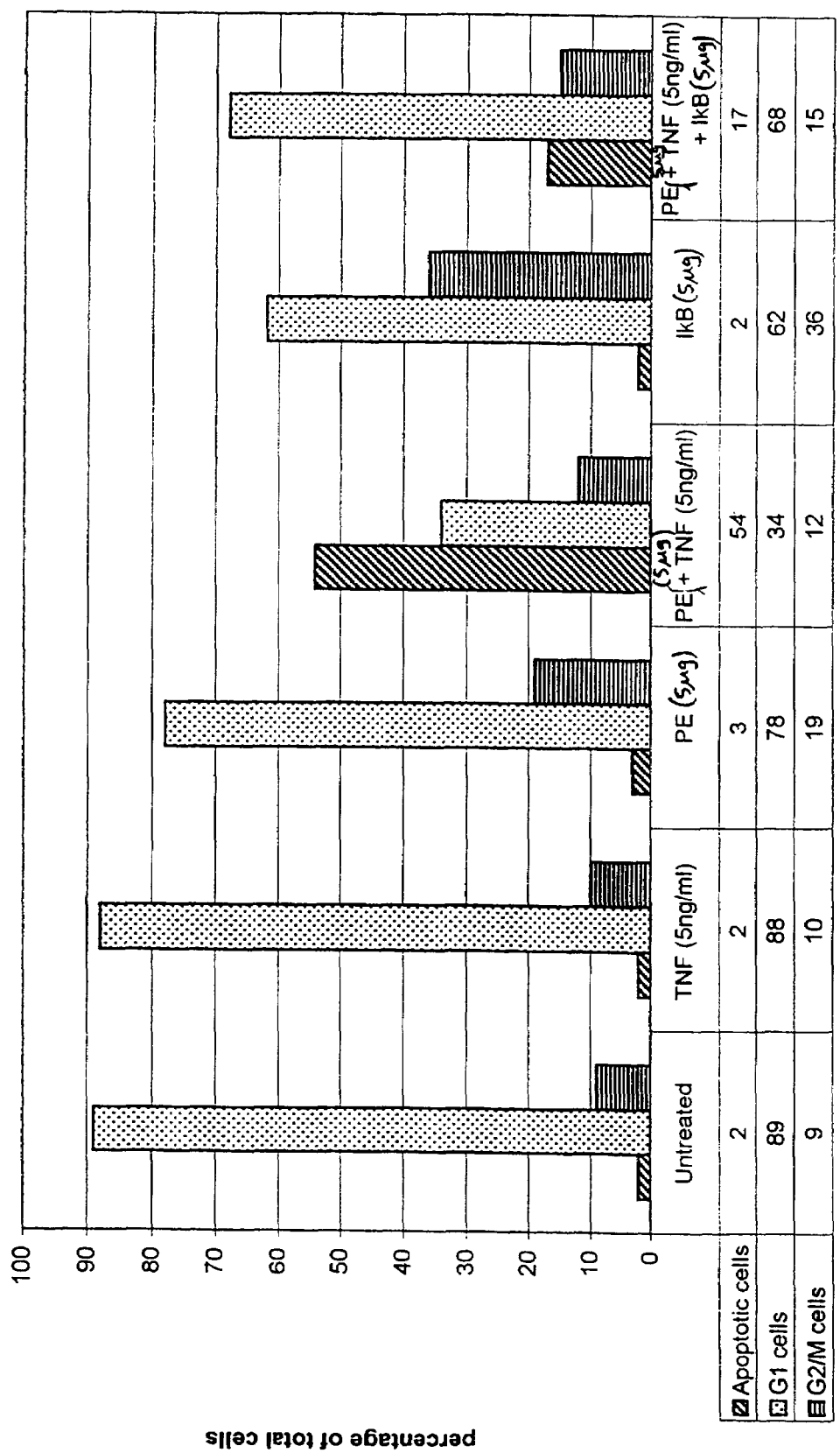
Figure 3:
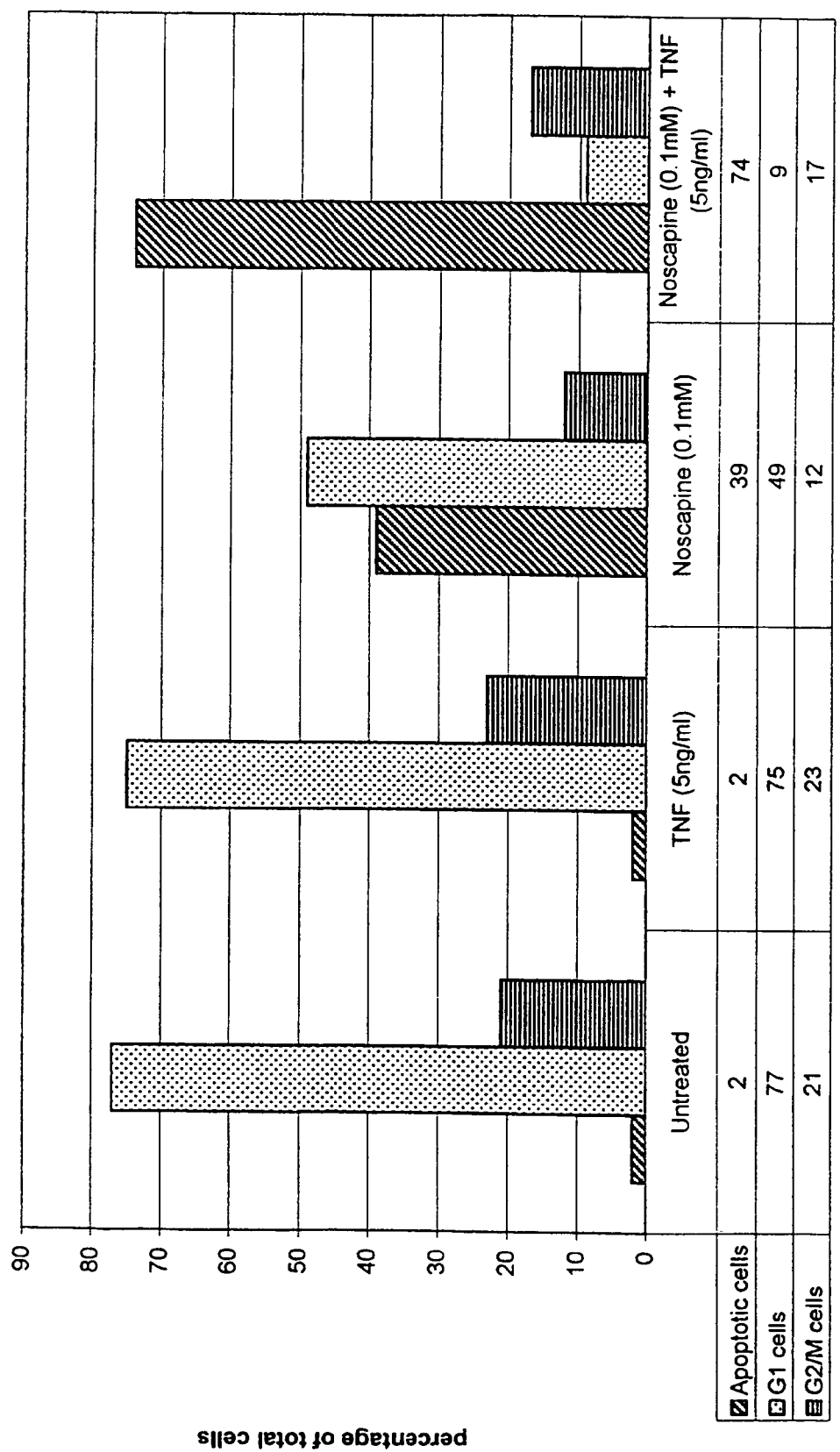
Figure 4:
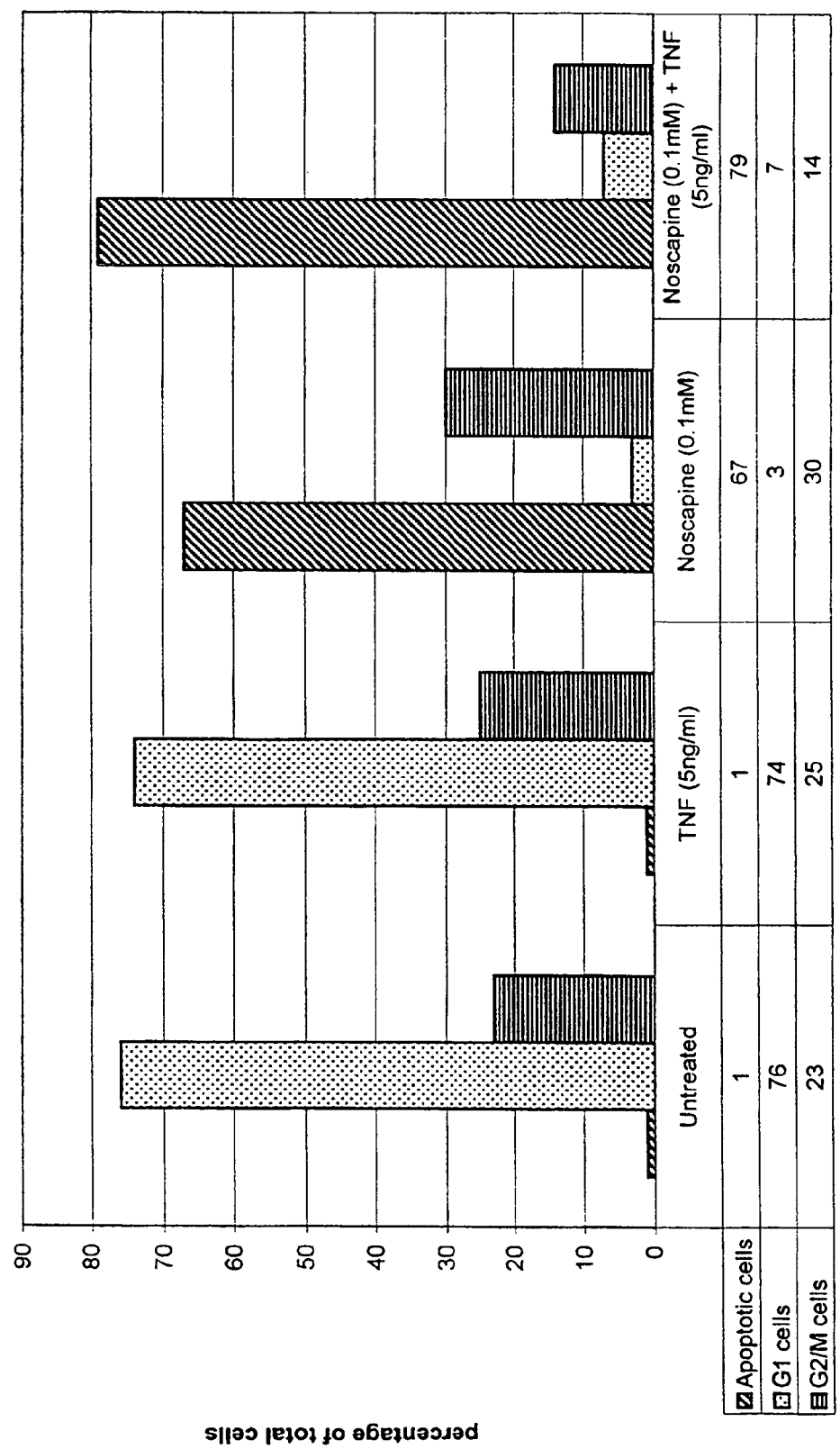
Figure 5A:
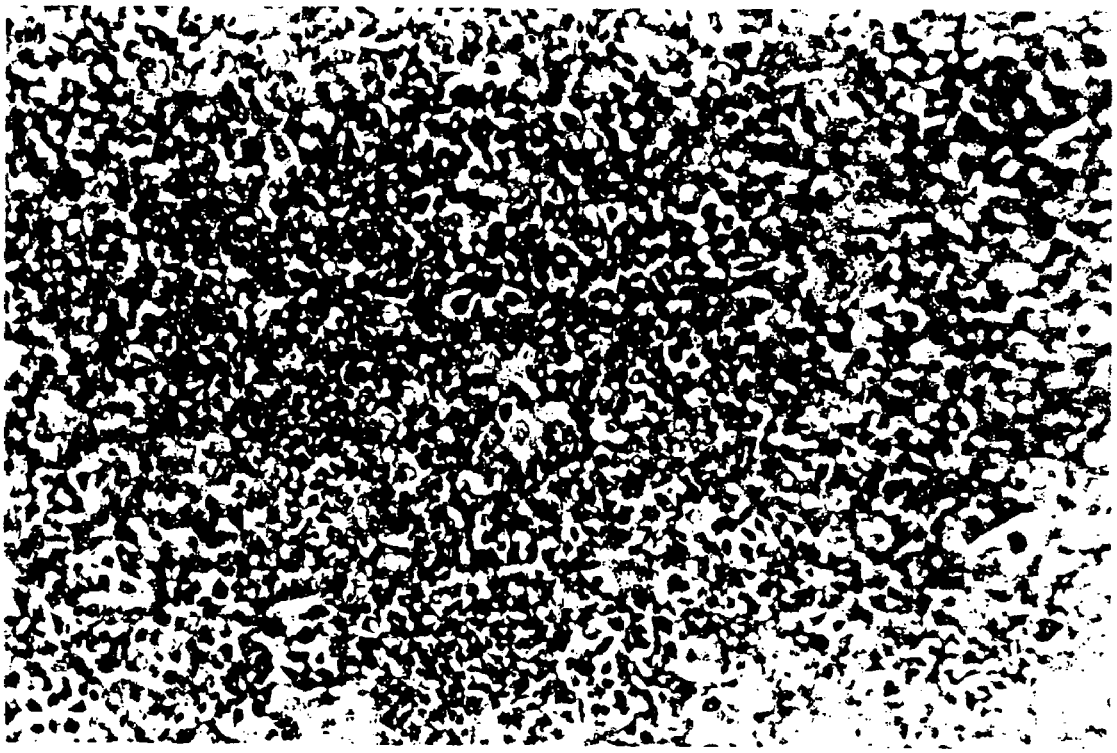
Figure 5B:
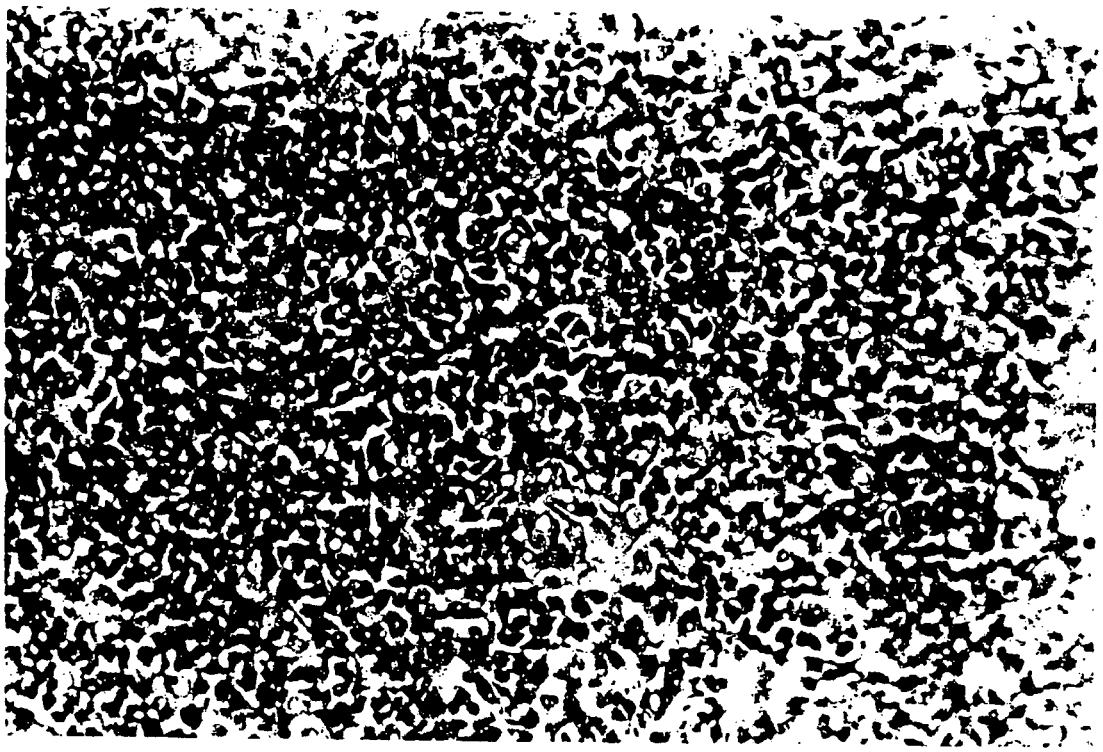
Figure 5C:
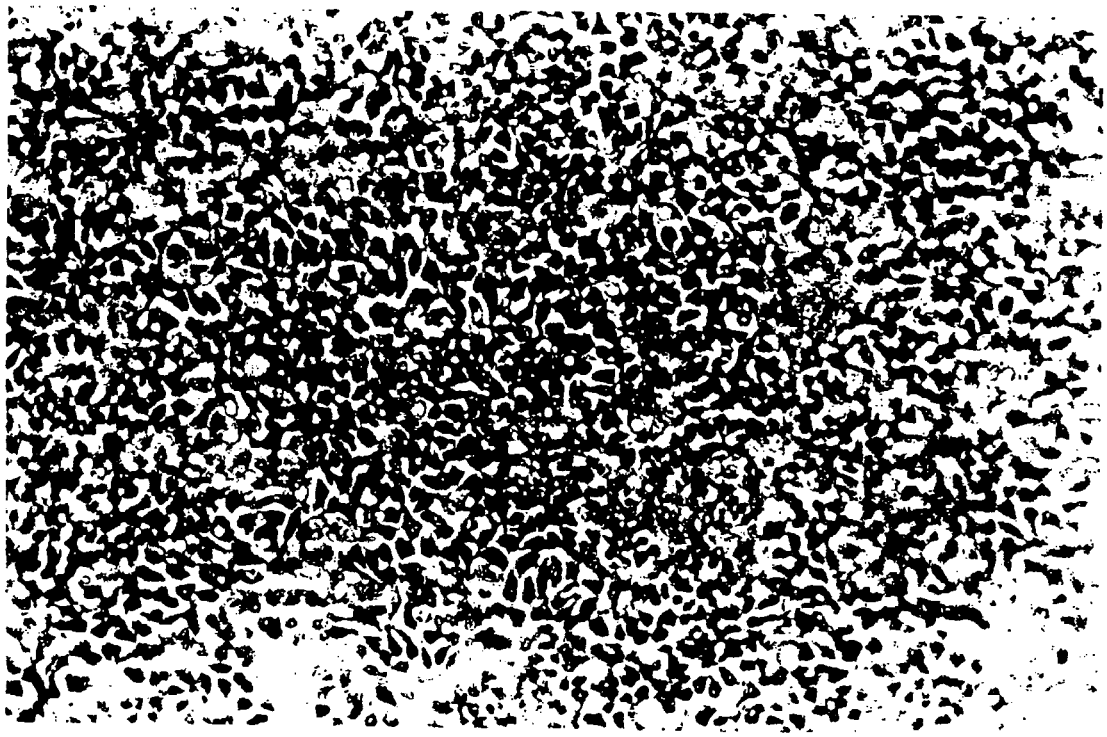
Figure 5D:
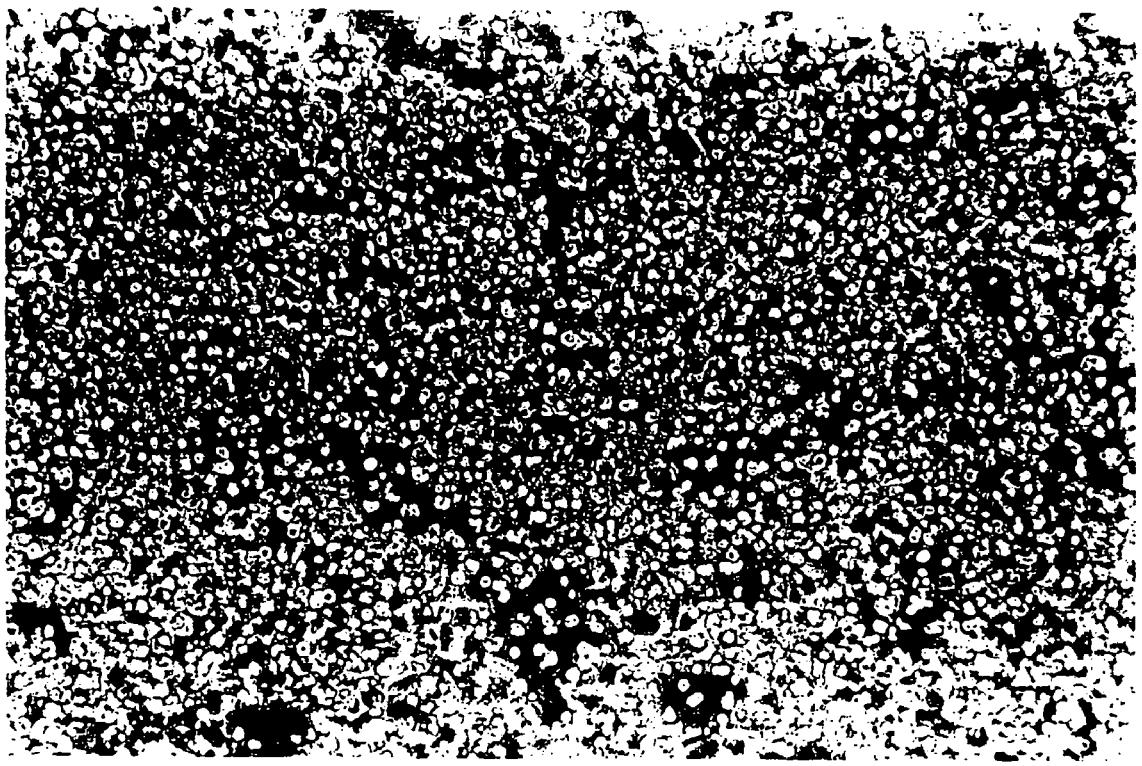
Figure 5E:
Figure 5F:
Figure 7A:
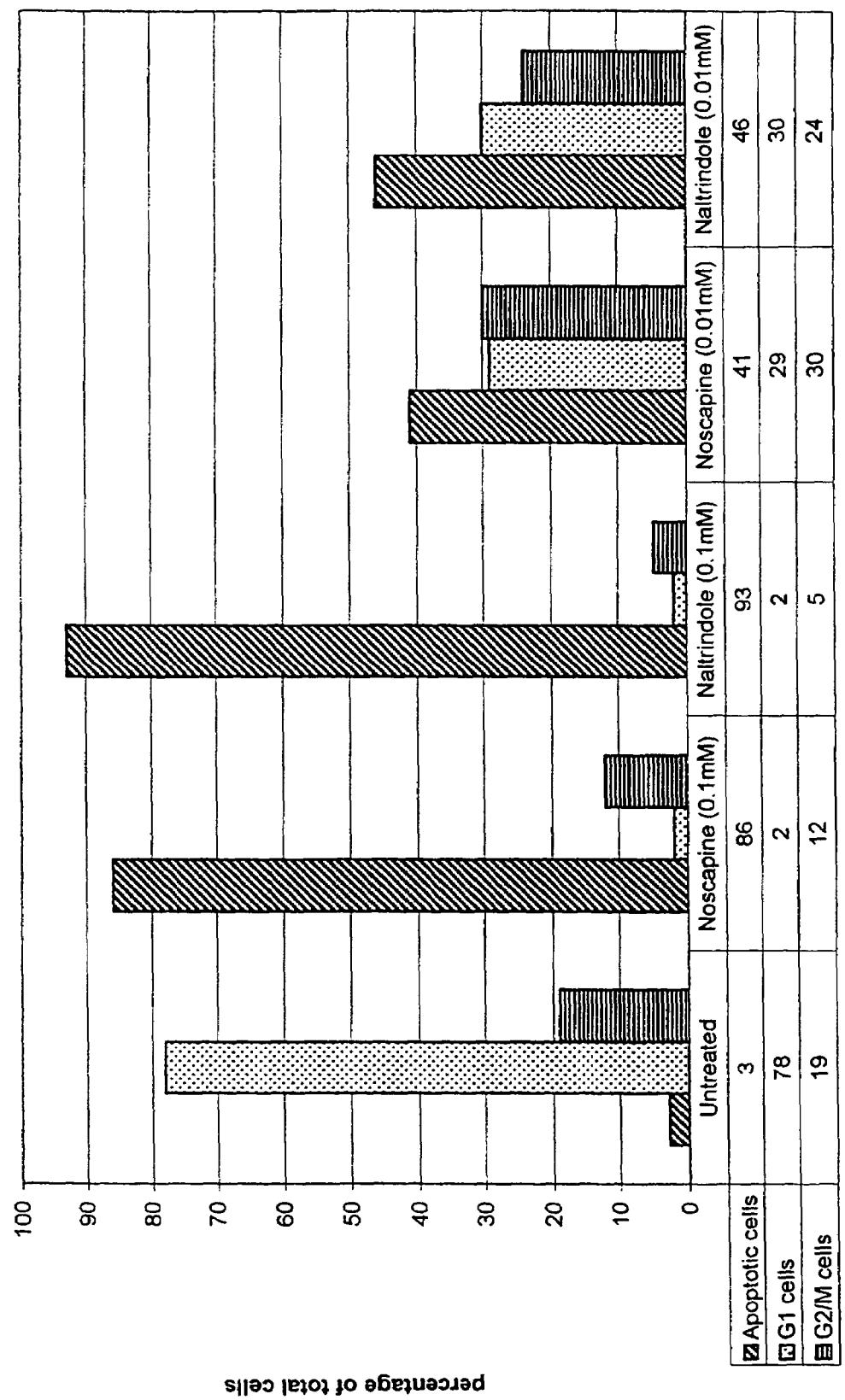
Figure 7B:
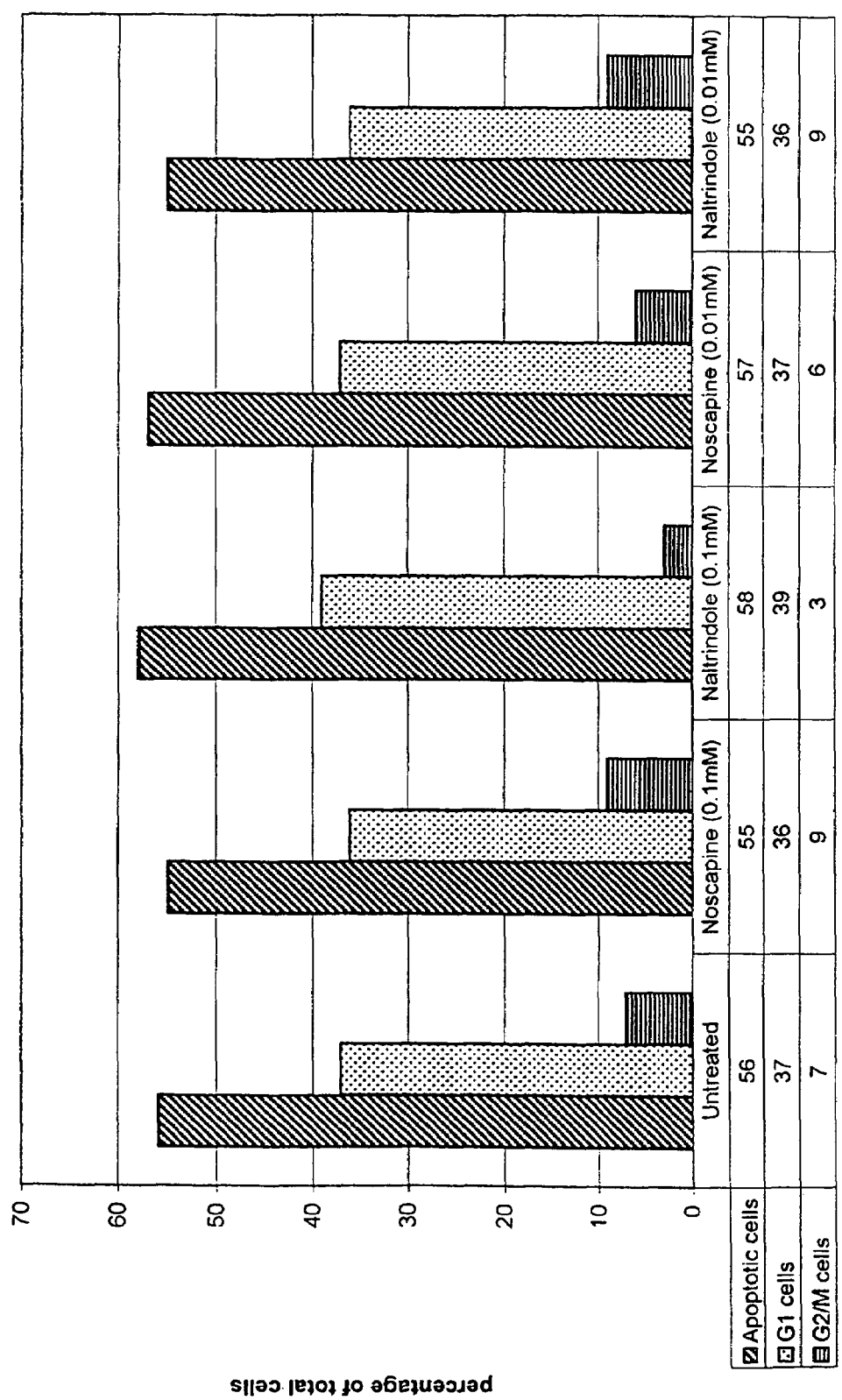
Figure 8:
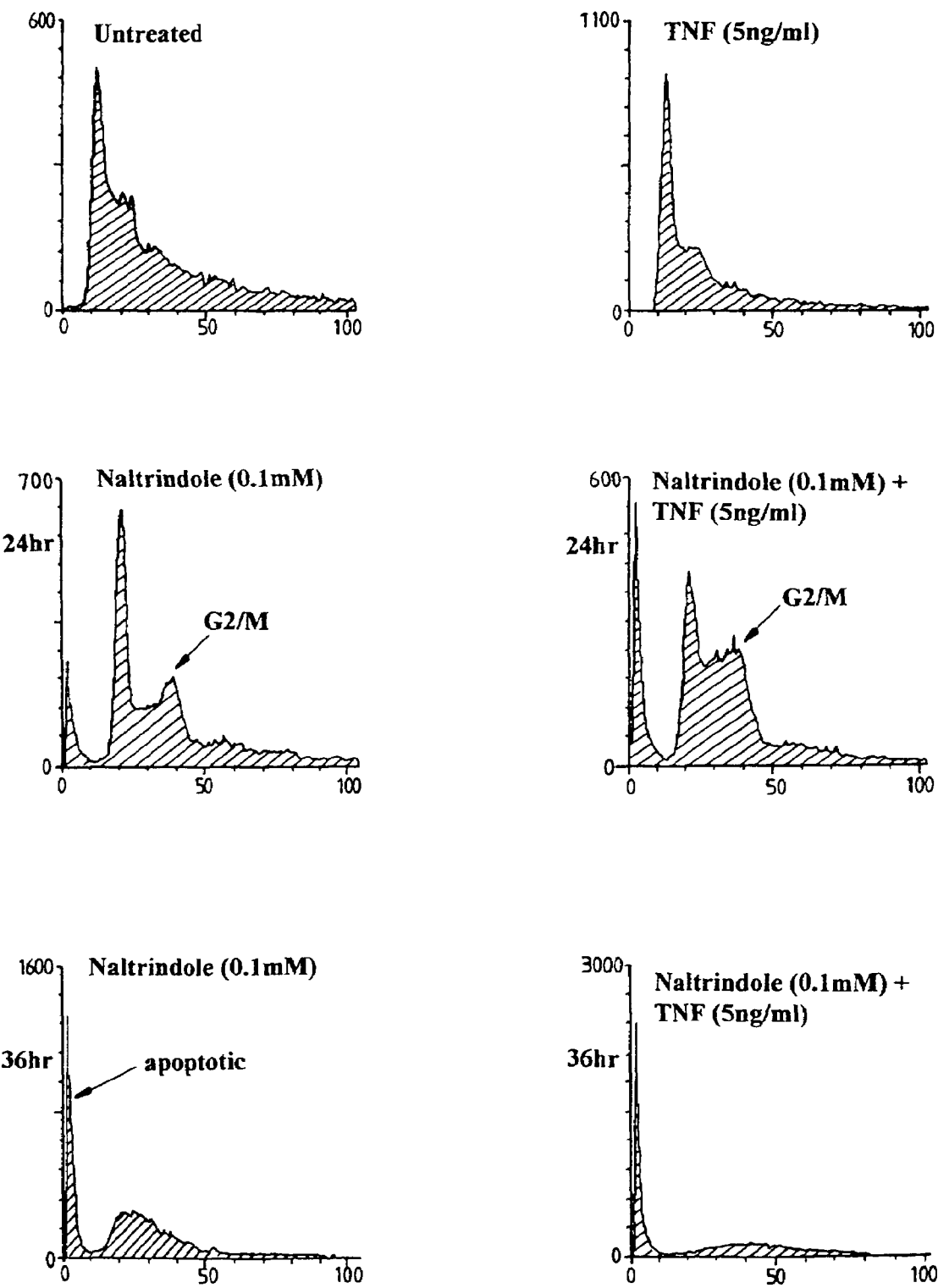
Figure 9A:
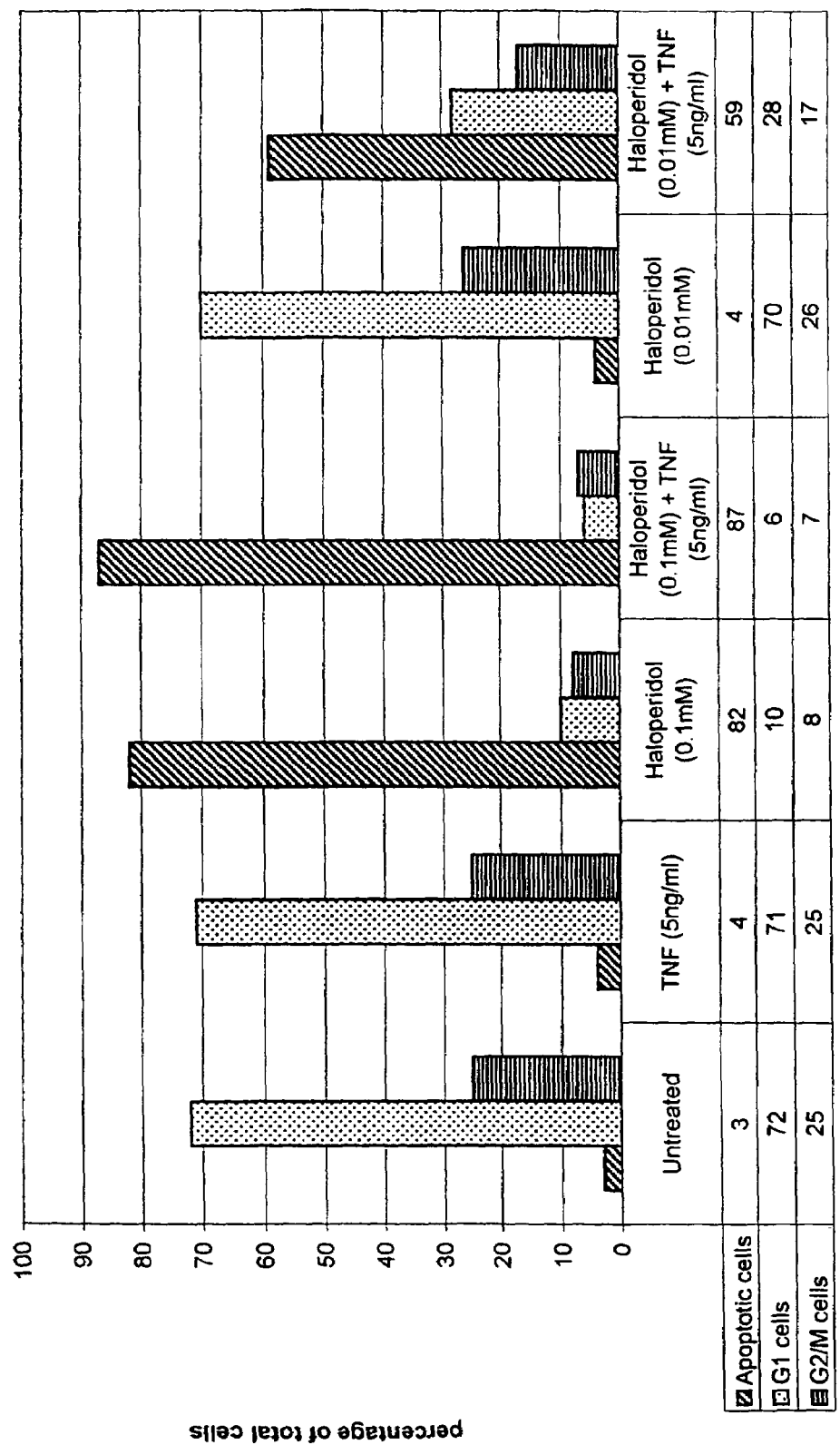
Figure 9B:
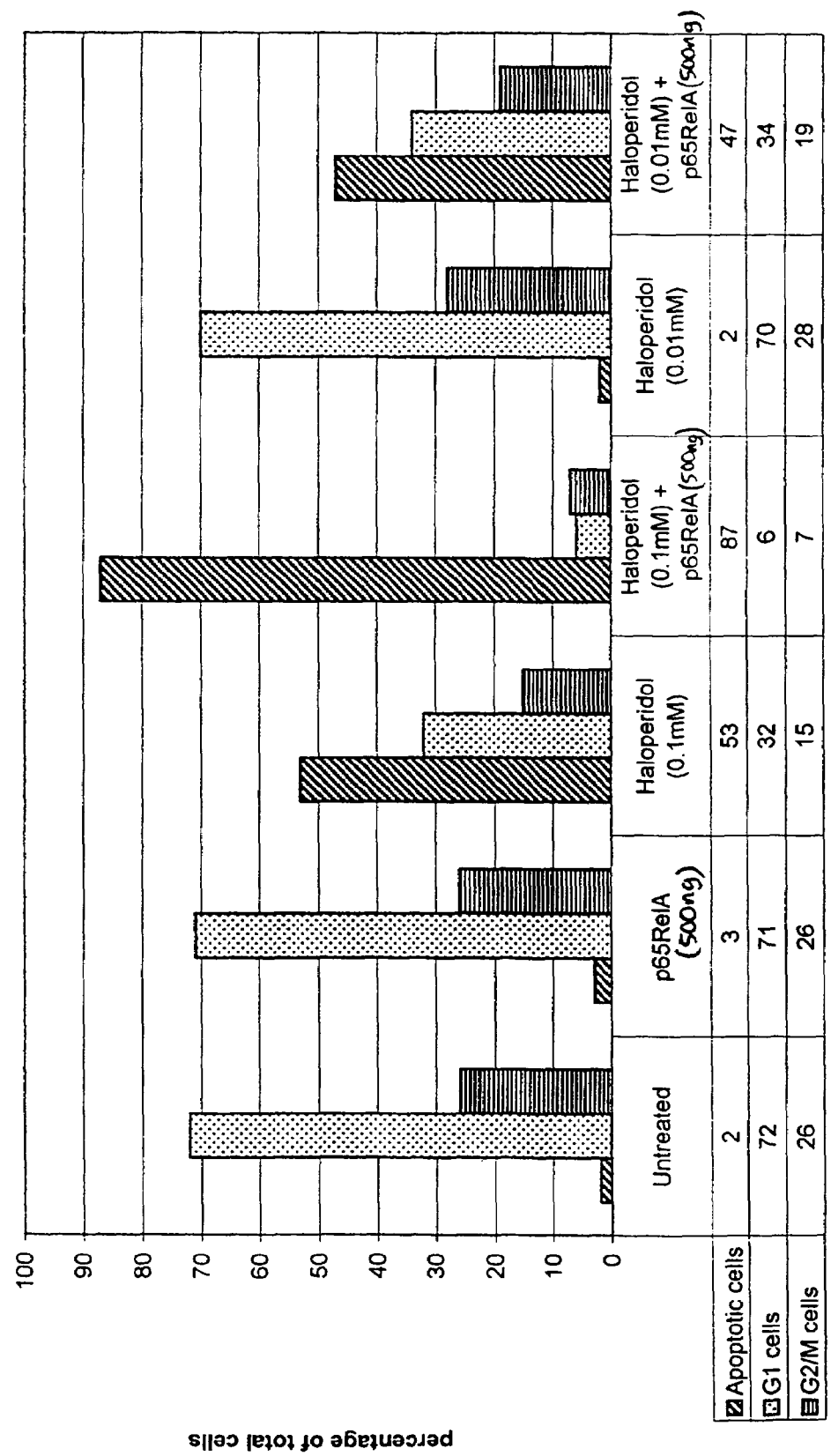
Figure 9C:
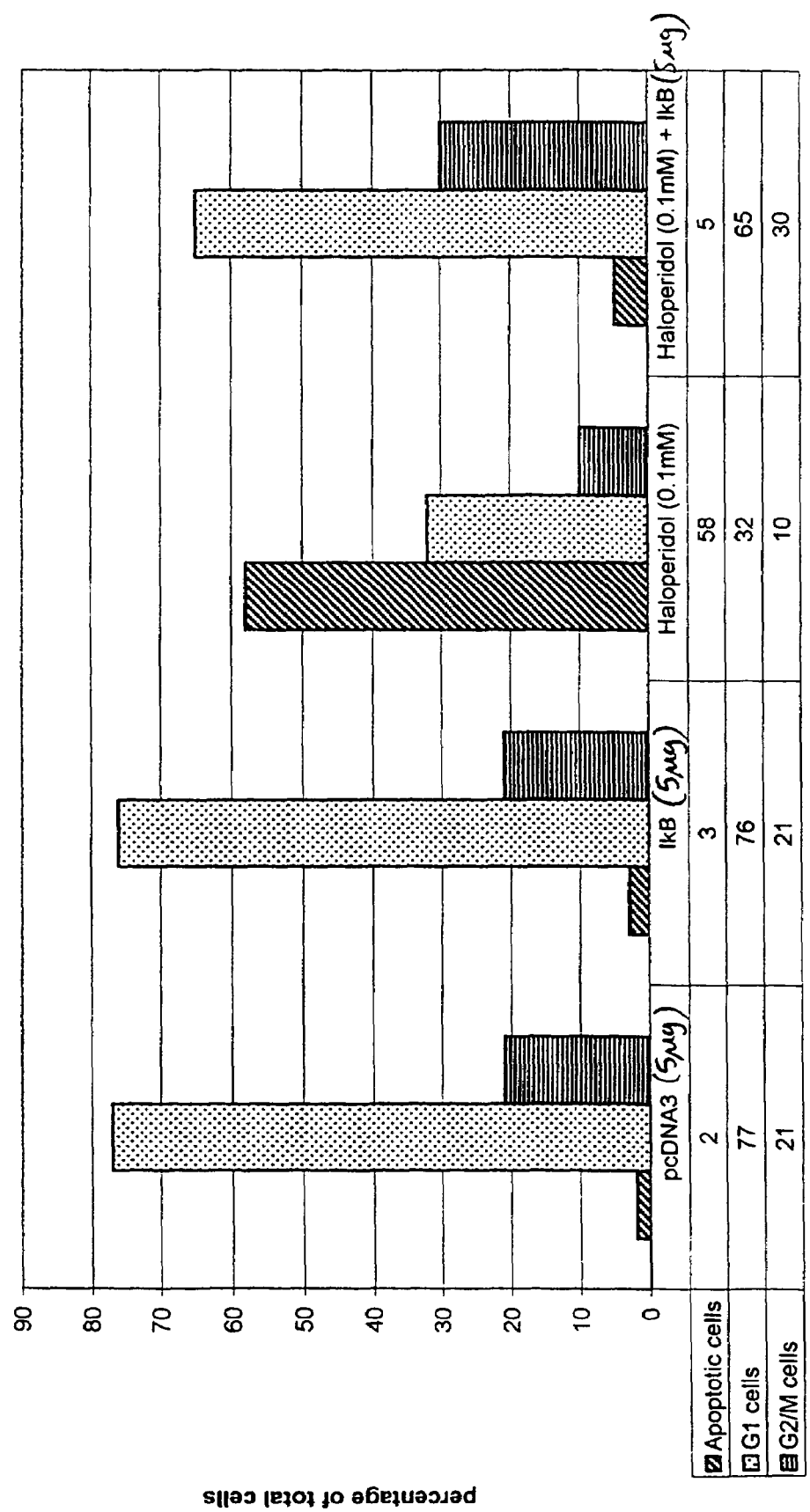
Figure 10A:
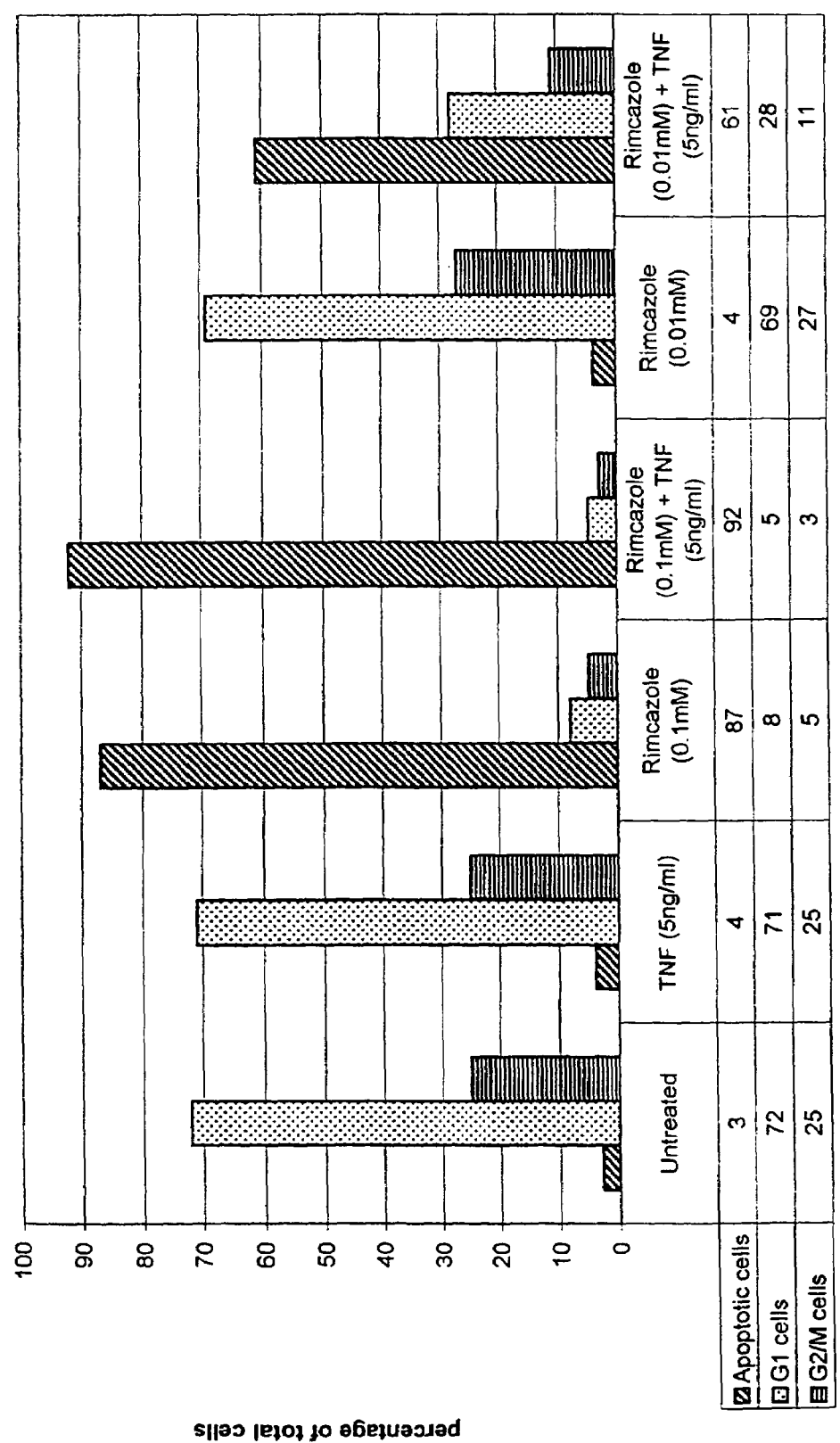
FIGS. 10a and 10b illustrate the induction of apoptotic death in lung cancer (H1299) cells by rimcazole.
Figure 10B:
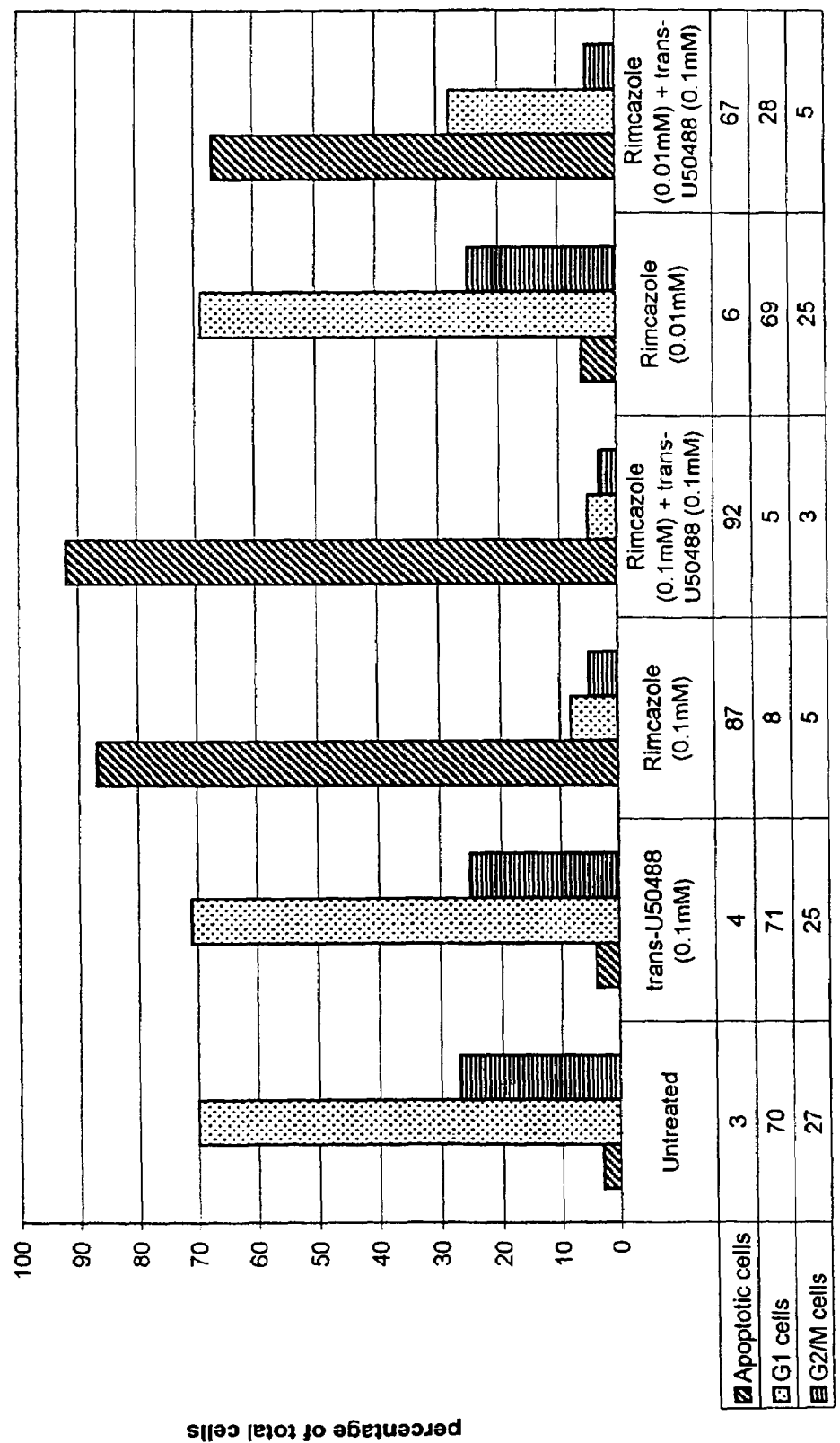
Figure 15B:
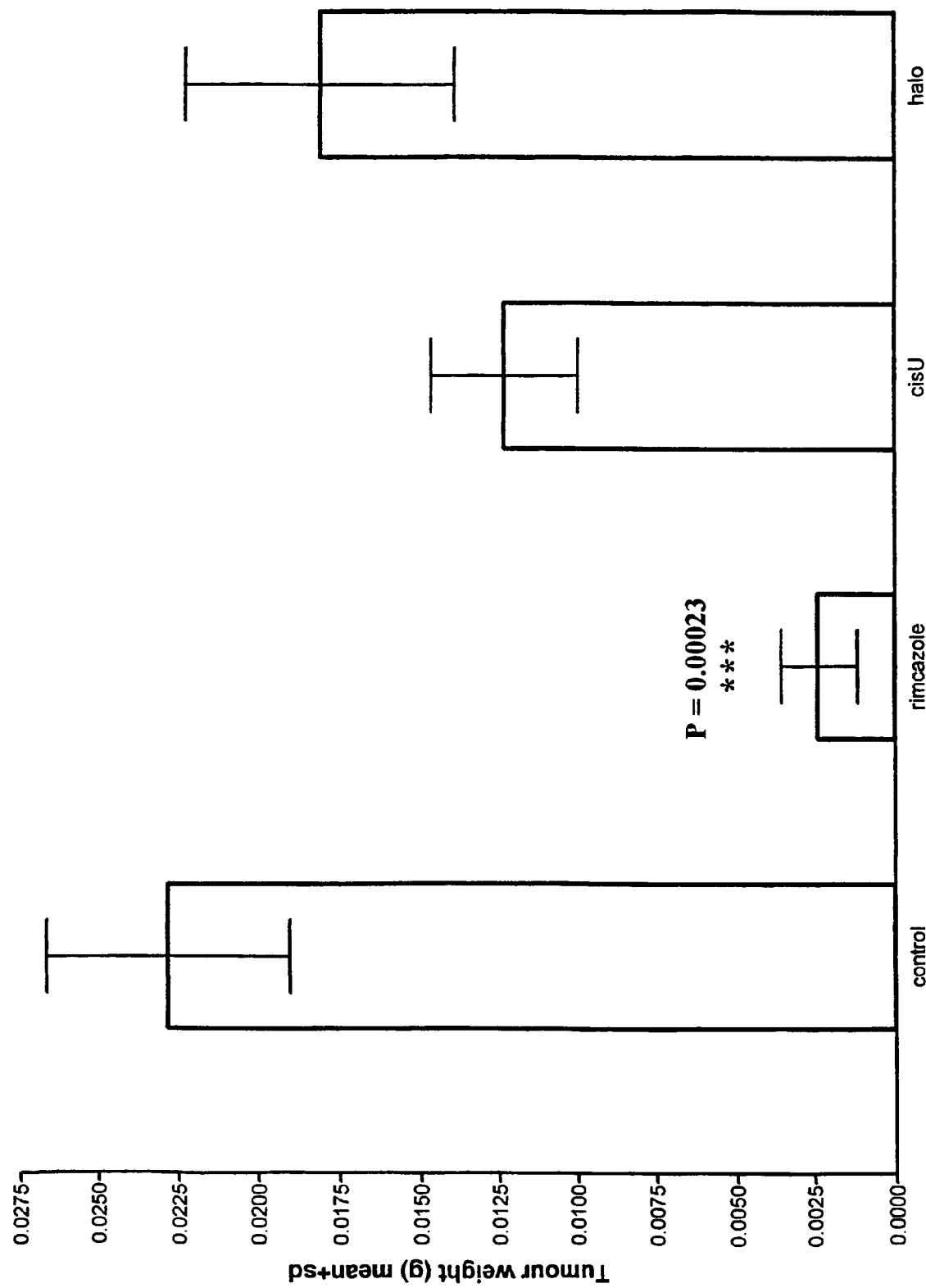
Figure 15C:
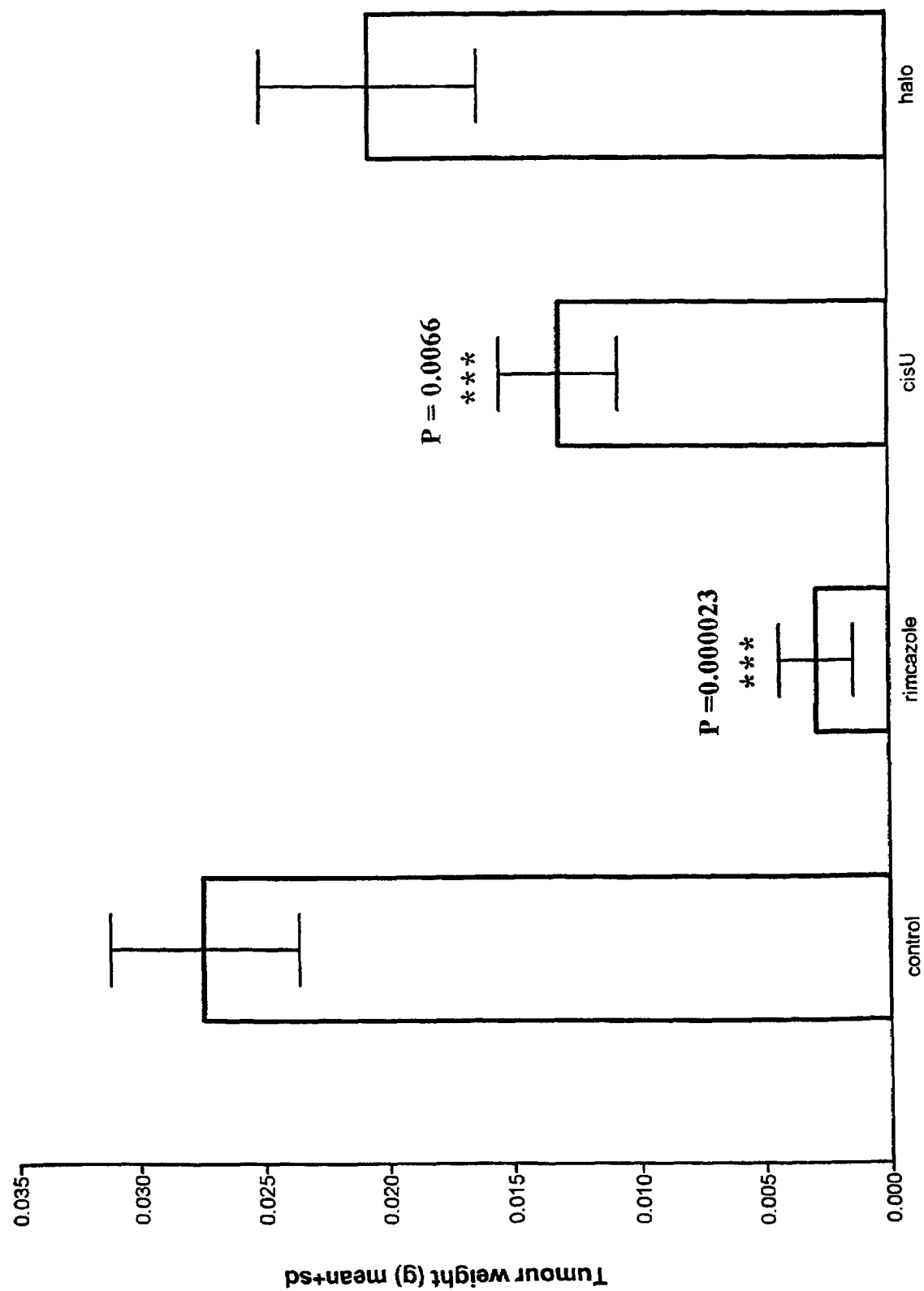

Mice tolerated the therapy well, with no ill effects except for transient sleepiness in the haloperidol treated groups. This is consistent with in vitro data described in Section 5 (FIG. 7) that tumour cells are preferentially affected by sigma ligands compared with normal cells. The tumour "take rate" (i.e. incidence of tumours developing from the total number of injected sites) was, as expected, less than 100%. Since therapy was initiated on day 0, preventing exclusion of "non-takes" prior to randomisation, the decision was taken to include analyses of both a) all tumour loci (FIG. 15b) and b) excluding sites which were negative at the second measurement on day 17 (FIG. 15c). The results are shown in FIG. 15a (mean tumour volume) and FIG. 15b&c (mean tumour weight +/−standard deviations). Mann Whitney U Tests (2 tailed) were carried out to compare tumour weights in treated (rimcazole, cis-U50488 or haloperidol) groups with tumour weights in the control group. Statistically significant effects (P value less than 0.05) are indicated by bars with asterisks (***).

Analysis of the results (based on tumour weights at excision) determined that rimcazole resulted in significant tumour growth inhibition (regardless of whether analysis included all or selected tumours). If the "non-takes" (did not appear to grow tumours) were excluded, cis U50488 also showed significant tumour growth inhibitory effects. Haloperidol also showed growth inhibition. These data confirm that sigma ligands, antagonistic and agonistic are potent anti-tumour agents in vivo, with no symptomatic evidence of toxicity. MDA MB 468 cells possess mutant p53 protein and are characteristic of advanced stage human breast cancer. Application of sigma ligands is therefore particularly applicable to this type of cancer.

APPENDIX 1

IUPAC chemical names for 1) named agents which induce apoptosis and 2) prototypic sigma ligands for assays to define sigma agents all obtainable from Sigma Ltd (Poole, Dorset, UK).

Naltrindole 4,8-methanobenzofuro[2,3-a]pyrido[4,3-b]carbazole-1,8a (9H)-diol,7-cyclopropylmethyl)-5,6,7,8,14,14b-hexahydro.

(CAS registry numbers 111469-81-9)

Trans-U50488 trans-3,4-Dichloro-N-Methyl-N-(2-[1-pyrrolidinyl]cyclohexyl)benzene-acetamide.

(CAS registry numbers 83913-06-8)

Noscapine (S-(R*,S*))-6,7-Dimethoxy-3-(5,6,7,8-tetrahydro-4-methoxy-6-methyl-1,3-dioxolo(4,5-g)isoquinolin-5-yl)-1(3H)-Isobenzofuranone.

(Cas Registry Numbers 128-62-1)

Haloperidol

4(4-(4-chlorophenyl)-4-hydroxy-1-piperidinyl)-1-(4-fluorophenyl)-1-Butanone.

(Cas Registry Numbers 52-86-8)

Rimcazole (BW234U)

cis-9-[3-(3,5-Dimethyl-1-piperazinyl)propyl]-9H-carbazole.

(CAS registry numbers 75859-04-0).

(+)-Pentazocine (+)-(2alpha,6alpha,11R*)-1,2,3,4,5,6-hexahydro-6,11-dimethyl-3-(3-methyl-2-butenyl)-2,6, -Methano-3-benzazocin-8-ol.

(CAS registry numbers 359-83-1)

DTG 1,3-Di(2-tolyl)guanidine.

(CAS registry numbers 97-39-2)

cis-U50488 is supplied from Sigma Ltd (Poole, Dorset, UK).

Tumour necrosis factor (TNF) is supplied by TCS Biologicals LTD (Buckingham, Bucks, UK).

Nocodazole, etoposide, colchicine, daunorubicin, podophyllotoxin and vinblastine are all supplied by Sigma Ltd (Poole, Dorset, UK).

Expression vectors encoding proenkephalin, p65 (RelA), IκB and p53 are all obtainable from MSI/WTB Complex, University of Dundee, Dundee, UK.

Agonistic anti CD40 antibody provides a means of stimulating B cells through CD40. A suitable antibody is available from PharMingen a Becton Dickinson Company, Becton Dickinson GmBH, HQ PharMingen Europe Cat. No. 33070D.

The invention claimed is:

1. A method for the preferential induction of apoptosis in a first population of cells in a human compared to a second population of cells in said human said method comprising exposing said first and second population of cells to at least one sigma receptor ligand, wherein said sigma receptor ligand produces a cytotoxic effect without chemical modification to impart a cytotoxic effect thereto, wherein the cells of said first population are tumour cells, wherein the cells of the first population are p53 null tumor cells, and said method further comprising exposing the cells to an agonist for a kappa receptor.

2. The method of claim 1, wherein the sigma receptor ligand is selected from the group consisting of haloperidol, rimcazole and cis-U50488.

3. The method of claim 1, wherein the cells of the first population are Hodgkin's lymphoma or late stage breast cancer.

4. The method of claim 1, wherein the cells of the first population are characterized by the presence of constitutively activated NF-κB in cells where it would not normally be found.

5. A method for the preferential induction of apoptosis in a first population of cells in a human compared to a second population of cells in said human said method comprising exposing said first and second population of cells to two different sigma receptor ligands, wherein said sigma receptor ligands produce a cytotoxic effect without chemical modification to impart a cytotoxic effect thereto, wherein the cells of said first population are tumour cells, and wherein the cells of the first population are p53 null tumor cells.

6. The method of claim 5, wherein the sigma receptor ligands are selected from the group consisting of haloperidol, rimcazole and cis-U50488.

7. A method for the preferential induction of apoptosis in a first population of cells in a human compared to a second population of cells in said human said method comprising exposing said first and second population of cells to at least one sigma receptor ligand, wherein said sigma receptor ligand produces a cytotoxic effect without chemical modification to impart a cytotoxic effect thereto, wherein the cells of said first population are tumour cells, wherein said sigma receptor ligand is rimcazole, wherein the cells of the first population are p53 null tumor cells.

8. A method for the preferential induction of apoptosis in a first population of cells in a human compared to a second population of cells in said human said method comprising exposing said first and second population of cells to two different sigma receptor ligands, wherein said sigma receptor ligands produce a cytotoxic effect without chemical modification to impart a cytotoxic effect thereto, wherein the cells of said first population are tumour cells, wherein the cells of the first population are characterized by the presence of constitutively activated NF-κB in cells where it would not normally be found.

9. The method of claim 8, wherein the cells of the first population are Hodgkin's lymphoma or late stage breast cancer.

10. The method of claim 8, wherein the sigma receptor ligands are selected from the group consisting of haloperidol, rimcazole and cis-U50488.

11. A method for the preferential induction of apoptosis in a first population of cells in a human compared to a second population of cells in said human said method comprising exposing said first and second population of cells to at least one sigma receptor ligand, wherein said sigma receptor ligand produces a cytotoxic effect without chemical modification to impart a cytotoxic effect thereto, wherein the cells of said first population are tumour cells, wherein said sigma receptor ligand is rimcazole, wherein the cells of the first population are characterized by the presence of constitutively activated NF-κB in cells where it would not normally be found.

12. The method of claim 11, wherein the cells of the first population are Hodgkin's lymphoma or late stage breast cancer.

\* \* \* \* \*